(12) United States Patent
Harada et al.

(10) Patent No.: US 6,333,109 B1
(45) Date of Patent: Dec. 25, 2001

(54) WATER-SWELLABLE CROSSLINKED POLYMER COMPOSITION AND PRODUCTION

(75) Inventors: Nobuyuki Harada, Suita; Shigeru Sakamoto, Himeji; Yoshifumi Adachi, Himeji; Toshimasa Kitayama, Himeji, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/371,956

(22) Filed: Aug. 11, 1999

(30) Foreign Application Priority Data

Aug. 13, 1998 (JP) ................................................. 10-228808
Aug. 17, 1998 (JP) ................................................. 10-230492
Sep. 1, 1998 (JP) ................................................. 10-246936

(51) Int. Cl.$^7$ ............................. B32B 15/02; C08G 63/48
(52) U.S. Cl. .............................. 428/402; 521/28; 525/57; 525/58; 524/599; 524/602; 428/500
(58) Field of Search ................................ 521/28; 525/57, 525/58; 524/599, 602; 428/402, 500

(56) References Cited

U.S. PATENT DOCUMENTS

| | | | |
|---|---|---|---|
| 4,818,598 | 4/1989 | Wong | 428/284 |
| 5,274,018 | 12/1993 | Tanaka et al. | 524/166 |
| 5,384,368 | 1/1995 | Date et al. | 525/186 |
| 5,804,605 | 9/1998 | Palumbo | 521/28 |
| 5,853,867 | 12/1998 | Harada et al. | 428/317.9 |

FOREIGN PATENT DOCUMENTS

| | | |
|---|---|---|
| 0493011 | 7/1992 | (EP) . |
| 0775161 | 5/1997 | (EP) . |
| 5838724 | 3/1983 | (JP) . |
| 62112654 | 5/1987 | (JP) . |
| 481468 | 3/1992 | (JP) . |
| 9615162 | 5/1996 | (WO) . |
| 9615163 | 5/1996 | (WO) . |
| 9615180 | 5/1996 | (WO) . |
| 9617681 | 6/1996 | (WO) . |
| 9824832 | 6/1998 | (WO) . |
| 9837149 | 8/1998 | (WO) . |
| 9925393 | 5/1999 | (WO) . |

*Primary Examiner*—Samuel A. Acquah
(74) *Attorney, Agent, or Firm*—Roylance, Abrams, Berdo & Goodman, L.L.P.

(57) ABSTRACT

The present invention has an object to provide a novel water-swellable crosslinked polymer composition which exhibits excellent saltwater absorption speed and capacity under a load. This object can be achieved in the case where, in a water-swellable crosslinked polymer composition comprising a blend of water-swellable crosslinked polymer particles of basicity in water and water-swellable crosslinked polymer particles of acidity in water, the water-swellable crosslinked polymer particles of basicity in water are unified with the water-swellable crosslinked polymer particles of acidity in water through ionic bondings in a state where water is present between the particles, wherein the ionic bondings are formed in a state where water is present between the particles by neutralization of at least part of acid groups of the water-swellable crosslinked polymer particles of acidity in water with the water-swellable crosslinked polymer particles of basicity in water.

31 Claims, 2 Drawing Sheets

US 6,333,109 B1

WATER-SWELLABLE CROSSLINKED POLYMER COMPOSITION AND PRODUCTION

TECHNICAL FIELD

The present invention relates to a water-swellable crosslinked polymer composition.

More specifically, the present invention relates to a novel water-swellable crosslinked polymer composition which comprises and exhibits an excellent saltwater absorption speed and has a greatly enhanced absorption capacity under a load.

BACKGROUND ART

In recent years, so-called water-absorbent polymers are widely used as constituent materials of sanitary materials, such as disposable diapers, sanitary napkins, and so-called incontinent pads, for the purpose of causing the water-absorbent polymers to absorb body fluids.

Known examples of the above water-absorbent polymers include: crosslinked products of partially neutralized polyacrylic acids; hydrolyzed products of starch-acrylic acid graft polymers; saponified products of vinyl acetate-acrylic acid ester copolymers; and hydrolyzed products of acrylonitrile- or acrylamide copolymers, and their crosslinked products. However, almost all of these conventionally known water-absorbent polymers are products by neutralizing their acid groups with compounds of alkaline metals. Therefore, in the case where the surface neighborhood of particles of the polymers is not secondarily crosslinked, their absorption capacity under a load for a physiological salt solution is below 10 g/g, and further, even if the surface neighborhood of particles of the polymers is secondarily crosslinked, their absorption capacity under a load for a physiological salt solution is merely 25 g/g at the highest, and is therefore still insufficient to the use for disposable diapers or sanitary articles. In addition, because those conventional water-absorbent polymers merely exhibit a remarkably low absorption capacity for aqueous liquids containing electrolytes, their application range is limited. Thus, it is desired to develop a novel salt-water-absorbing agent which can rapidly absorb salt water to swell therewith even under loaded conditions.

To solve such problems, WO 96/15162, WO 96/15180, WO 96/17681, WO 98/24832, and WO 98/37149 propose water-absorbing agents which comprise water-swellable crosslinked polymers of acidity in water and compounds of basicity in water and utilize the ion-exchanging function and desalting mechanism due to interactions between the acid and the base. However, processes as described in these patents have problems in that: because the compound of basicity in water and the water-swellable crosslinked polymer of acidity in water are allowed to exist separately from each other, the saltwater absorption speed under a load is slow, and further, the absorption capacity under a load is low.

DISCLOSURE OF THE INVENTION

OBJECT OF THE INVENTION

An object of the present invention is to provide: a novel water-swellable crosslinked polymer composition which can rapidly absorb salt water to swell therewith even under loaded conditions; and a production process therefor. Accordingly, if the water-swellable crosslinked polymer composition according to the present invention is used as a water-absorbing agent for absorbent articles such as disposable diapers, the leakage can be remarkably decreased and their surfaces can be kept in a rustling dry state, even in the case of a long-term use.

SUMMARY OF THE INVENTION

The present inventors diligently studied to provide the novel water-swellable crosslinked polymer composition which can achieve the above object. As a result, the inventors attained to the present invention.

That is to say, the following inventions are described herein:

(First invention): A water-swellable crosslinked polymer composition, which comprises a blend of a water-swellable crosslinked polymer of acidity in water and a water-swellable crosslinked polymer of basicity in water, with the composition being characterized by exhibiting a saltwater absorption capacity of at least 50 g/g under a load of 3.5 g/cm$^2$ in 10 hours, and absorbing 60% of the 10-hour saltwater absorption capacity under the load of 3.5 g/cm$^2$ in less than 5 minutes.

(Second invention): A water-swellable crosslinked polymer composition, which comprises a blend of a water-swellable crosslinked polymer of acidity in water and a water-swellable crosslinked polymer of basicity in water, with the composition being characterized by exhibiting a saltwater absorption capacity of at least 40 g/g under a load of 21 g/cm$^2$ in 10 hours, and absorbing 60% of the 10-hour saltwater absorption capacity under the load of 21 g/cm$^2$ in less than 5 minutes.

(Third invention): A water-swellable crosslinked polymer composition, which comprises a blend of water-swellable crosslinked polymer particles of acidity in water and water-swellable crosslinked polymer particles of basicity in water, with the composition being characterized in that the water-swellable crosslinked polymer particles of acidity in water are unified with the water-swellable crosslinked polymer particles of basicity in water through ionic bondings in a state where water is present between the particles, and further characterized by exhibiting a saltwater absorption capacity of not less than 33 g/g in 60 minutes.

(Fourth invention): A water-swellable crosslinked polymer composition, which comprises a blend of water-swellable crosslinked polymer particles of acidity in water and water-swellable crosslinked polymer particles of basicity in water, with the composition being characterized in that ionic bondings are formed in a state where water is present between the particles by neutralization of at least part of acid groups of the water-swellable crosslinked polymer particles of acidity in water with the water-swellable crosslinked polymer particles of basicity in water, and further characterized by exhibiting an absorption capacity of not less than 25 g/g under a load.

(Fifth invention): A water-swellable crosslinked polymer composition, which comprises a blend of a water-swellable crosslinked polymer of acidity in water and a water-swellable crosslinked polymer of basicity in water, with the composition being characterized in that the water-swellable crosslinked polymer of acidity in water is a crosslinked polyacrylic acid, and in that the water-swellable crosslinked polymer of basicity in water is a crosslinked polyethylenimine and/or a crosslinked polyallylamine, and further characterized by exhibiting a desalting amount of not less than 0.35 g/g.

(Sixth invention): A production process for a water-swellable crosslinked polymer composition including a blend of water-swellable crosslinked polymer particles of acidity in water and water-swellable crosslinked polymer particles of basicity in water, with the process being characterized by comprising the step of adding the water-swellable crosslinked polymer particles of basicity in water to the water-swellable crosslinked polymer particles of acidity in water, thereby neutralizing at least part of acid groups of the water-swellable crosslinked polymer particles of acidity in water to form ionic bondings in a state where water is present between the particles.

(Seventh invention): A production process for a water-swellable crosslinked polymer composition including a blend of a water-swellable crosslinked polymer of acidity in water and a water-swellable crosslinked polymer of basicity in water, with the process being characterized by comprising the step of blending the water-swellable crosslinked polymer of acidity in water and the water-swellable crosslinked polymer of basicity in water under conditions where at least one of the water-swellable crosslinked polymer of acidity in water and the water-swellable crosslinked polymer of basicity in water is in a hydrogelled state, and further characterized in that both the water-swellable crosslinked polymer of acidity in water and the water-swellable crosslinked polymer of basicity in water have an extractable content of not more than 10 weight % before blending.

(Eighth invention): A production process for a water-swellable crosslinked polymer of acidity in water, comprising the steps of: carrying out aqueous solution polymerization of a polymerizable monomer in the presence of a copolymerizable crosslinking agent, wherein the polymerizable monomer contains at least one acid group selected from the group consisting of carboxylic acid groups, sulfonic acid groups, and phosphoric acid groups, and 80 to 100 mol % of the acid groups in the polymerizable monomer are present in the acid form; and heating the resultant hydrogelled polymer at a temperature of not lower than 100° C. so that the water content in the polymer will be in the range of 1 to 20 weight % (but not including 20 weight %); and further, if necessary, pulverizing the heated polymer.

DETAILED DESCRIPTION OF THE INVENTION

It has been found that, surprisingly, a water-swellable crosslinked polymer composition which is remarkably excellent in the saltwater absorption speed under a load and in the absorption capacity under a load can be obtained in the case where, in a water-swellable crosslinked polymer composition comprising a blend of water-swellable crosslinked polymer particles of basicity in water and water-swellable crosslinked polymer particles of acidity in water, the water-swellable crosslinked polymer particles of basicity in water are unified with the water-swellable crosslinked polymer particles of acidity in water through ionic bondings in a state where water is present between the particles, wherein the ionic bondings are formed in a state where water is present between the particles by neutralization of at least part of acid groups of the water-swellable crosslinked polymer particles of acidity in water with the water-swellable crosslinked polymer particles of basicity in water. In addition, it has further been found that the above water-swellable crosslinked polymer composition which is remarkably excellent in the saltwater absorption speed under a load and in the absorption capacity under a load can easily be obtained by a production process comprising the step of adding water-swellable crosslinked polymer particles of basicity in water to water-swellable crosslinked polymer particles of acidity in water, thereby neutralizing at least part of acid groups of the water-swellable crosslinked polymer particles of acidity in water to form ionic bondings in a state where water is present between the particles, or by a production process comprising the step of blending a water-swellable crosslinked polymer of acidity in water and a water-swellable crosslinked polymer of basicity in water under conditions where at least one of the water-swellable crosslinked polymer of acidity in water and the water-swellable crosslinked polymer of basicity in water is in a hydrogelled state, wherein both the water-swellable crosslinked polymer of acidity in water and the water-swellable crosslinked polymer of basicity in water have an extractable content of not more than 10 weight % before blending.

Hereinafter, the present invention is explained in detail.

In the present invention, the water-swellable crosslinked polymer of acidity in water is a water-swellable crosslinked polymer which exhibits acidity in pure water and is crosslinked to such an extent that it can absorb pure water to swell therewith. In the present invention, the water-swellable crosslinked polymer of acidity in water, for example, exhibits a pKa of preferably 2~12, more preferably 3~8, in pure water and an absorption capacity of preferably not less than 1 g/g, more preferably not less than 5 g/g, for pure water. In the case where the pKa value or the absorption capacity for pure water is out of these ranges, it might be impossible to achieve effects of the present invention. Examples of the water-swellable crosslinked polymer of acidity in water, showing the above property values, include water-swellable crosslinked polymers that contain acid groups (of which 50~100 mol %, more preferably 70~100 mol %, still more preferably 80~100 mol %, most preferably 90~100 mol %, are present in the acid form) and are crosslinked slightly to such an extent that they can be water-insoluble.

In the present invention, more preferably usable examples of the water-swellable crosslinked polymer of acidity in water include water-swellable crosslinked polymers that contain at least one acid group selected from the group consisting of carboxylic acid groups, sulfonic acid groups, and phosphoric acid groups. In the present invention, the water-swellable crosslinked polymer of acidity in water, for example, can be obtained by conventional processes, such as a) a process comprising the step of introducing a crosslinked structure into the resultant polymer when polymerizing an acid-group-containing polymerizable monomer, and b) a process comprising the step of post-crosslinking an acid-group-containing polymer resultant from the polymerization of the acid-group-containing polymerizable monomer. In addition, the water-swellable crosslinked polymer of acidity in water, usable in the present invention, may be a crosslinked polypeptide, such as a crosslinked product of polyaspartic or polyglutamic acid, or an acid water-swellable crosslinked polymer, as derived from a natural product, such as crosslinked carboxymethyl cellulose.

The post-crosslinking treatment of the acid-group-containing polymer in process b) above, for example, can be achieved by processes to introduce a crosslinked structure into the polymer, such as I) a process involving heat treatment, II) a process involving the irradiation of radiations such as electron beams and gamma rays, III) a process involving the use of a compound having, per molecule, at least two functional groups reactable upon a functional group of the acid-group-containing polymer, such as (poly) ethylene glycol diglycidyl ether, glycerol diglycidyl ether, (poly)ethylene glycol, (poly)propylene glycol, glycerol, pentaerythritol, ethylenediamine, polyethylenimine, and ethylene carbonate.

In the present invention, an example of more preferably usable production processes for the water-swellable crosslinked polymer of acidity in water is the above process a) comprising the step of introducing a crosslinked structure into the resultant polymer when polymerizing an acid-group-containing polymerizable monomer, in view of the ease of controlling the resulting degrees of polymerization and crosslinking.

In the present invention, preferably usable examples of the acid-group-containing polymerizable monomer include: polymerizable monomers containing a carboxylic acid group, such as acrylic acid, methacrylic acid, ethacrylic acid, crotonic acid, sorbic acid, maleic acid, itaconic acid, and cinnamic acid, and their anhydrides; polymerizable monomers containing a sulfonic acid group, such as vinylsulfonic acid, allylsulfonic acid, styrenesulfonic acid, vinyltoluenesulfonic acid, 2-(meth)acrylamido-2-methylpropanesulfonic acid, 2-(meth)acryloylethanesulfonic acid, and 2-(meth)acryloylpropanesulfonic acid; and polymerizable monomers containing a phosphoric acid group, such as 2-hydroxyethylacryloyl phosphate, 2-hydroxyethylmethacryloyl phosphate, phenyl-2-acryloyloxyethyl phosphate, and vinyl phosphate. These acid-group-containing monomers may be used either alone respectively or in combinations with each other. Among them, preferable ones are polymerizable monomers containing a carboxylic or sulfonic acid group, particularly preferably, a carboxylic acid group, and the most preferable is acrylic acid. Thus, the most preferable water-swellable crosslinked polymer of acidity in water is a crosslinked polyacrylic acid.

In the present invention, if necessary, other polymerizable monomers can be used along with the above acid-group-containing monomer. Examples of such other polymerizable monomers include: alkyl esters or alkylene oxide esters of unsaturated carboxylic acids (e.g. acrylic acid, methacrylic acid, ethacrylic acid, crotonic acid, sorbic acid, maleic acid, itaconic acid, cinnamic acid), such as methyl (meth)acrylate, ethyl (meth)acrylate, methoxypolyethylene glycol (meth) acrylate, and polyethylene glycol mono(meth)acrylate; aromatic vinyl hydrocarbons, such as styrene; aliphatic vinyl hydrocarbons, such as ethylene, propylene, and butene; unsaturated nitriles, such as acrylonitrile; and unsaturated amides, such as acrylamide and methacrylamide.

In the present invention, a process comprising the step of polymerizing an acid-group-containing polymerizable monomer in the presence of a copolymerizable crosslinking agent is preferable as the above process comprising the step of introducing a crosslinked structure into the resultant polymer when polymerizing an acid-group-containing polymerizable monomer, However, a self-crosslinking structure to form a crosslinked structure even without the above copolymerizable crosslinking agent is also available.

In the present invention, preferably usable examples of the copolymerizable crosslinking agent, which is copolymerizable with the acid-group-containing polymerizable monomer, include: compounds (1) having at least two polymerizable double bonds; and compounds (2) having at least one polymerizable double bond and at least one functional group reactive upon the monomer.

Specific examples of compound (1) above include the following: N,N'-methylenebis(meth)acrylamide, N,N'-methylenebis(N-vinylalkylamide), (poly)ethylene glycol di(meth)acrylate, (poly)propylene glycol di(meth)acrylate, trimethylolpropane tri(meth)acrylate, trimethylolpropane di(meth)acrylate, glycerol tri(meth)acrylate, glycerol acrylate methacrylate, ethylene-oxide-denatured trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly (meth)allyloxyalkanes, divinylbenzene, divinyltoluene, divinylxylene, divinylnaphthalene, divinyl ether, divinyl ketone, trivinylbenzene, tolylene diisocyanate, hexamethylene diisocyanate; acetals, such as tetraallyloxyethane; ethers, such as pentaerythritol tetraallyl ether, pentaerythritol triallyl ether, pentaerythritol diallyl ether, trimethylolpropane triallyl ether, trimethylolpropane diallyl ether, ethylene glycol diallyl ether, diethylene glycol diallyl ether, triethylene glycol diallyl ether, and (poly)allyl ethers as derived from compounds having two or more hydroxyl groups per molecule such as monosaccharides, disaccharides, polysaccharides, and cellulose.

Examples of compound (2) above include: compounds having an epoxy group and a polymerizable double bond in a molecule, such as glycidyl (meth)acrylate; compounds having a hydroxy group and a polymerizable double bond in a molecule, such as N-methylol(meth)acrylamide; unsaturated compounds containing a primary to quaternary amino group, such as N,N,N-trimethyl-N-(meth)acryloyloxyethyltrimethylammonium chloride, N,N,N-triethyl-N-(meth)acryloyloxyethyltrimethylammonium chloride, dimethylaminoethyl(meth)acrylate, diethylaminoethyl(meth)acrylate, allylamine, and vinylpyridine.

Among the copolymerizable crosslinking agents, preferable ones are: bis(meth)acrylamide; di- or poly-esters from polyols and unsaturated monocarboxylic acids; and polyallyl compounds. A particularly preferable one is at least one member selected from the group consisting of N,N'-methylenebisacrylamide, trimethylolpropane tri(meth)acrylate, (poly)ethylene glycol diacrylate, triallylamine, and poly(meth)allyloxyalkanes.

In the present invention, the amount of the copolymerizable crosslinking agent is usually in the range of 0.001~10%, preferably 0.01~5 %, of the total weight of the entire polymerizable monomers and the copolymerizable crosslinking agent. In the case where the amount of the copolymerizable crosslinking agent is smaller than 0.001%, the resultant polymer might merely exhibit low gel strength when absorbing water. In the case where the amount exceeds 10%, the absorption capacity might be low.

The amount of other polymerizable monomers, as used if necessary, is usually not larger than 40%, preferably not larger than 20%, of the total weight of the entire polymerizable monomers and the copolymerizable crosslinking agent.

Incidentally, when the polymerization is carried out, it is permitted to add to the polymerizable monomer the following compounds: hydrophilic polymers, such as starch (including derivatives thereof), cellulose (including derivatives thereof), polyvinyl alcohol, polyacrylic acid, and crosslinked polyacrylic acid; chain transfer agents, such as hypophosphorous acid (or its salts); and water-soluble or water-dispersible surfactants. Incidentally, these compounds, which may be added to the polymerizable monomer, are for example disclosed in U.S. Pat. Nos. 4,076,663, 4,320,040, 4,833,222, 5,118,719, 5,149,750, 5,154,713, 5,264,495, EP 0372981, and EP 0496594.

In the present invention, bulk polymerization or precipitation polymerization is, for example, available as the method to polymerize the acid-group-containing monomer or as the method to polymerize the acid-group-containing monomer and the copolymerizable crosslinking agent, and further, other polymerizable monomers as used if necessary. However, considering the performance or the easiness of the polymerization control, it is preferable to carry out aqueous solution polymerization or reversed-phase suspension polymerization using the monomer in the form of its aqueous solution. Incidentally, examples of solvents, usable for this aqueous solution polymerization or reversed-phase suspension polymerization, include water, methanol, ethanol, acetone, N,N-dimethylformamide, dimethyl sulfoxide, methyl ethyl ketone, and any mixture thereof. When the solvent is used, the concentration of the acid-group-containing monomer is not especially limited, but is usually not less than 10%, preferably in the range of 15~80 %, on the weight basis. In addition, the polymerization temperature is usually in the range of 0~150° C., preferably 10~100° C.

In addition, the method of initiating the polymerization may be conventional polymerization methods, for example, involving the use of radical polymerization catalysts or the irradiation of such as radiations, electron beams, or ultraviolet rays.

As to the method involving the use of radical polymerization catalysts, examples of those catalysts include: inorganic peroxides, such as potassium persulfate, ammonium persulfate, and sodium persulfate; organic peroxides, such as t-butyl hydroperoxide, hydrogen peroxide, benzoyl peroxide, and cumene hydroperoxide; and azo compounds, such as 2,2'-azobis(2-amidinopropane) dihydrochloride, azoisobutyronitrile, and azobiscyanovaleric acid. When oxidizable radical polymerization catalysts such as peroxides are used, they may be combined with reductants, such as sodium sulfite, sodium hydrogensulfite, ferrous sulfate, and L-ascorbic acid, to carry out redox polymerization. In addition, it is also permitted to use the radical polymerization catalysts jointly with each other. Furthermore, it is permitted that the amount of the radical polymerization catalyst, as used, is a conventional one. For example, the radical polymerization catalyst is used in the ratio of usually 0.0005~5%, preferably 0.0001~1%, of the total weight of the entire polymerizable monomers and the copolymerizable crosslinking agent.

In the present invention, the water-swellable crosslinked polymer of basicity in water is a water-swellable crosslinked polymer which exhibits basicity in pure water and is crosslinked to such an extent that it can absorb pure water to swell therewith. In the present invention, the water-swellable crosslinked polymer of basicity in water, for example, exhibits a pKb of preferably 2~12, more preferably 3~8, in pure water and an absorption capacity of preferably not less than 1 g/g, more preferably not less than 5 g/g, for pure water. In the case where the pKb value or the absorption capacity for pure water is out of these ranges, it might be impossible to achieve effects of the present invention. Examples of the water-swellable crosslinked polymer of basicity in water, showing the above property values, include water-swellable crosslinked polymers that contain basic groups (of which 50~100 mol %, more preferably 70~100 mol %, most preferably 90~100 mol %, are present in the basic form) and are crosslinked slightly to such an extent that they can be water-insoluble. In the present invention, more preferably usable examples of the water-swellable crosslinked polymer of basicity in water include crosslinked polymers containing a primary to tertiary amino group, in which 50~100 mol % of the basic groups are present in the basic form, and which are crosslinked slightly to such an extent that they can be water-insoluble.

Examples thereof include: crosslinked polyalkyleneamine, crosslinked polyvinylamine, crosslinked polyallylamine, crosslinked poly(N-vinylimidazole), crosslinked polyvinylpyridine, crosslinked poly(vinylpyridineamine oxide), crosslinked polydiallylamine, crosslinked polyamidepolyamine, crosslinked poly(dimethylaminoalkyl acrylate), crosslinked poly(dimethylaminoalkyl methacrylate), crosslinked polydimethylaminoalkylacrylamide, crosslinked polydimethylaminoalkylmethacrylamide, crosslinked polyamidine, crosslinked poly(hydrazineacrylic acid), crosslinked asparagic acid-hexamethylenediamine polycondensation products, crosslinked basic polyamino acids (e.g. polylysine), crosslinked chitosan, and copolymers of these polymers. These need to exhibit water-swellability and be crosslinked to such an extent that they can be water-insoluble. The water-swellable crosslinked polymer of basicity in water is preferably a crosslinked polymer containing an amino group, more preferably, at least one member selected from the group consisting of crosslinked polyethylenimine, crosslinked polyallylamine, crosslinked poly(N-vinylimidazole), crosslinked polyvinylpyridine, crosslinked poly(vinylpyridineamine oxide), crosslinked polyamidine, crosslinked poly(hydrazineacrylic acid), and crosslinked polydiallylamine, and most preferably, at least one member selected from the group consisting of crosslinked polyethylenimine and crosslinked polyallylamine.

The water-swellable crosslinked polymer of basicity in water, as used in the present invention, can be obtained by introducing a crosslinked structure into a polymer by conventional processes, for example, a process in which, when polymerized, the corresponding basic-group-containing monomer is copolymerized with another copolymerizable crosslinking agent, thereby forming a crosslinked polymer, or a process in which the basic-group-containing polymer is crosslinked with a crosslinking agent having at least two groups reactable upon a functional group (e.g. amino group) of the basic-group-containing polymer. When the above functional group is an amino group, usable examples of the crosslinking agent include compounds that are conventionally used and have per molecule at least two groups, such as epoxy groups, aldehyde groups, alkyl halide groups, isocyanate groups, carboxyl groups, acid anhydride groups, acid halide groups, ester bonding moieties, and active double bonds. Examples of such a crosslinking agent include bisepoxy compounds, epichlorohydrin, dihalides (e.g. dibromoethylene), formalin, dialdehyde compounds (e.g. glyoxal), diglycidyl ethers of (poly)ethylene glycols, diglycidyl ethers of (poly)propylene glycols, diglycidyl ethers of dihydric alcohols (e.g. neopentyl alcohol), polyglycidyl ethers of glycerol, methylenebisacrylamide, and diacrylate compounds, but there is no limitation thereto. The kind and the amount of the crosslinking agent are selected in view of factors such as absorption capacity or strength of the resultant water-swellable crosslinked polymer of basicity in water, but, when the basic-group-containing polymer is a polymer containing an amino group, the amount is preferably in the range of 0.001~20 mol % of the amine unit of the polymer. In the case where the amount of the crosslinking agent is smaller than 0.001 mol %, the absorption capacity of the resultant water-swellable crosslinked polymer is low, and further, its strength is insufficient. In the case where the amount is larger than 20 mol %, the absorption capacity might be low.

In the present invention, as to the shape of the water-swellable crosslinked polymer of basicity in water when blending this polymer with the water-swellable crosslinked polymer of acidity in water, various shapes are available, such as irregular pulverized shapes, spherical shapes, fibrous shapes, bar shapes, nearly spherical shapes, and flat shapes. However, preferable examples of the water-swellable crosslinked polymer of basicity in water include surfactant-free and truly or nearly spherical crosslinked polyethylenimine particles, particles with irregular pulverized shapes, or granulated products of these particles (or hydrogels thereof), as disclosed in the specification of U.S. patent application Ser. No. 287509 (filed Apr. 7, 1999).

As to the ratio between the water-swellable crosslinked polymer of acidity in water and the water-swellable crosslinked polymer of basicity in water in the water-swellable crosslinked polymer composition according to the present invention, it is preferable that both polymers are used such that the pH in water of the water-swellable crosslinked polymer composition, comprising a unified product of both polymers, can fall in the neutral region (pH 6~8). In the case where the pH is below 6 or above 8, there might be disadvantages in that the saltwater absorption speed and the saltwater absorption capacity under a load are low, or in that there are problems on the safety to human skins. Accordingly, the ratio between the polymers, as used, is determined by the fundamental molecular weight and the acidity of the water-swellable crosslinked polymer of acidity in water and by the fundamental molecular weight and the basicity of the water-swellable crosslinked polymer of basicity in water. However, the weight ratio of the water-swellable crosslinked polymer of basicity in water to the water-swellable crosslinked polymer of acidity in water is preferably in the range of 1:0.25~1:4. Furthermore, when the water-swellable crosslinked polymer of basicity in water is the crosslinked polyethylenimine and when the water-swellable crosslinked polymer of acidity in water is the crosslinked polyacrylic acid, the above weight ratio is preferably in the range of 1:0.5~1:3. In addition, when the water-swellable crosslinked polymer of basicity in water is the crosslinked polyallylamine and when the water-swellable crosslinked polymer of acidity in water is the crosslinked polyacrylic acid, the above weight ratio is preferably in the range of 1:0.75~1:4.

The water-swellable crosslinked polymer composition, according to the fourth present invention, comprises a blend of water-swellable crosslinked polymer particles of acidity in water and water-swellable crosslinked polymer particles of basicity in water, and has ionic bondings as are formed in a state where water is present between the particles by neutralization of at least part of acid groups of the water-swellable crosslinked polymer particles of acidity in water with the water-swellable crosslinked polymer particles of basicity in water, and further, this composition exhibits an absorption capacity of not less than 25 g/g under a load, wherein the absorption capacity under a load is preferably not less than 27 g/g, and more preferably not less than 30 g/g.

In the present invention, the "ionic bondings are formed in a state where water is present between the particles by neutralization of part of acid groups of the water-swellable crosslinked polymer particles of acidity in water with the water-swellable crosslinked polymer particles of basicity in water" means that: for example, when the water-swellable crosslinked polymer composition according to the present invention is particulate, each particle thereof comprises the water-swellable crosslinked polymer of acidity in water and the water-swellable crosslinked polymer of basicity in water, and both polymers are bonded to each other by partial neutralization of acid functional groups with basic functional groups which are present in respective surfaces of the polymers, and, in a dry state, both polymers exist as one particle without easily separating from each other, and, also in a wet state, both polymers behave as one particle without breaking the bondings between them. In the present invention, for obtaining excellent desalting effects, it is preferable that only the ionic bondings are formed between the particles. The ionic bondings can be confirmed from a fact that, when immersed in a solution of high or low pH, the water-swellable crosslinked polymer composition according to the present invention can be separated into the water-swellable crosslinked polymer of acidity in water and the water-swellable crosslinked polymer of basicity in water. In addition, for example, the state where both polymers are bonded to each other can also be observed with a micrograph of each particle by coloring the composition with indicators which get colored on acidity and basicity respectively.

The water-swellable crosslinked polymer composition, according to the third present invention, comprises a blend of water-swellable crosslinked polymer particles of acidity in water and water-swellable crosslinked polymer particles of basicity in water, wherein the water-swellable crosslinked polymer particles of acidity in water are unified with the water-swellable crosslinked polymer particles of basicity in water through ionic bondings in a state where water is present between the particles, and further, this composition exhibits a saltwater absorption capacity of not less than 33 g/g in 60 minutes, wherein the saltwater absorption capacity in 60 minutes is preferably not less than 35 g/g.

The "unification through ionic bondings in a state where water is present between the particles," as referred to in the present invention, means that: for example, when the water-swellable crosslinked polymer composition according to the present invention is particulate, each particle thereof comprises the water-swellable crosslinked polymer of acidity in water and the water-swellable crosslinked polymer of basicity in water, wherein, in a dry state, both polymers exist as one particle without easily separating from each other, and, also in a wet state, both polymers are ionically bonded to each other and behave as one particle. In the present invention, for obtaining excellent desalting effects, it is preferable that only the ionic bondings are formed between the particles. How things stand in the unification through ionic bondings in a state where water is present between the particles can be confirmed by the above method. In addition, the state of being bonded by unification can also be observed with an electron micrograph of each particle.

The above water-swellable crosslinked polymer composition, according to the fourth present invention, is obtainable in accordance with the sixth present invention, namely, by a process comprising the step of adding the water-swellable crosslinked polymer particles of basicity in water to the water-swellable crosslinked polymer particles of acidity in water, thereby neutralizing at least part of acid groups of the water-swellable crosslinked polymer particles of acidity in water to form ionic bondings in a state where water is present between the particles. In addition, the above water-swellable crosslinked polymer composition, according to the third present invention, is obtainable by a process comprising the step of blending the water-swellable crosslinked polymer of basicity in water and the water-swellable crosslinked polymer of acidity in water in the presence of water so that too much force may not be applied to them.

In such a process, in the present invention, it is important to bond the water-swellable crosslinked polymer of acidity in water and the water-swellable crosslinked polymer of basicity in water to each other surely in a uniform ratio. For achieving this, it is preferable that the blending of both polymers is carried out in the presence of a solvent, such as water, to partially neutralize them or to unify them, rather than in a dry state. Generally, in the case where both polymers are blended in a dry state, the water-swellable crosslinked polymer of acidity in water and the water-swellable crosslinked polymer of basicity in water are not present in a uniform ratio, so that a composition with a low absorption capacity under a load is merely obtained. When the solvent such as water is used, it is preferable to obtain the water-swellable crosslinked polymer composition via a drying step. More specifically, it is preferable to blend the polymers under conditions where at least one of them is not dry, but hydrous in accordance with the seventh present invention, or to add water and then blend the polymers when blending the polymers under conditions where both of them are dry. The presence of water can produce ionic bondings in surfaces of both crosslinked polymers to strongly bond both crosslinked polymers to each other, thereby obtaining a water-swellable crosslinked polymer composition which does not easily separate even due to mechanical impact in the steps following the drying step, such as pulverization or transportation step, but keeps a constantly uniform blended state. In addition, the partial bonding and the neighboring of both crosslinked polymers would efficiently cause the ion-exchanging and desalting functions as made by interactions between the polymers, and thereby greatly enhance the absorption capacity under a load and the saltwater absorption speed under a load.

For the above blending step, in the present invention, the following blending methods are both available: (1) a method in which the water-swellable crosslinked polymer of basicity in water and the water-swellable crosslinked polymer of acidity in water are blended under conditions where at least one of the water-swellable crosslinked polymer of basicity in water and the water-swellable crosslinked polymer of acidity in water is in a hydrogelled state (seventh present invention), and (2) a method in which a dry water-swellable crosslinked polymer of basicity in water and a dry water-swellable crosslinked polymer of acidity in water are blended, and then water is added to further blend them, wherein the "water-swellable crosslinked polymer which is in a hydrogelled state" is a water-swellable crosslinked polymer which has a water content of not less than 20 weight %, preferably of not less than 50 weight %, more preferably of 70~90 weight %, and wherein the "dry water-swellable crosslinked polymer" is a water-swellable crosslinked polymer which has a water content less than 20 weight %.

In method (1) above, it is important that both the water-swellable crosslinked polymer of acidity in water and the water-swellable crosslinked polymer of basicity in water have an extractable content of not more than 10 weight % before blending. In the present invention, it is important to blend both water-swellable crosslinked polymers so that too much force to keep the particle shapes previous to blending may not be applied. In the case where at least one of the water-swellable crosslinked polymers has an extractable content more than 10 weight %, too much force is applied when blending, therefore the particle shapes previous to blending cannot be kept, and the number of effective functional groups in the water-swellable crosslinked polymer of acidity in water and the water-swellable crosslinked polymer of basicity in water is reduced, so no excellent desalting effects can be exhibited. In addition, both water-swellable crosslinked polymers cause the swelling restriction which lowers the saltwater absorption capacity.

For blending both polymers not to apply too much force to the water-swellable crosslinked polymer particles, it is necessary to fitly control the blending pressure dependently on factors such as water content or properties (e.g. gel strength or extractable content) of the hydrogel, but it is usually preferable to blend both polymers so that the applied force due to blending may be a facial pressure less than 50 $kg/cm^2$ or a linear pressure less than 25 kg/cm. In the case where the applied force due to blending is a facial pressure of not less than 50 $kg/cm^2$ or a linear pressure of not less than 25 kg/cm, there are disadvantages in that bondings (e.g. IPN) other than ionic bondings are formed between particles, thus resulting in the reduction of the desalting amount. The pressure range to blend both polymers is more preferably a facial pressure less than 10 $kg/cm^2$ or a linear pressure less than 5 kg/cm, and still more preferably a facial pressure less than 5 $kg/cm^2$ or a linear pressure less than 1 kg/cm. For achieving the blending at such a low pressure, it is preferable to use blenders such as kneaders or meat choppers, wherein the meat choppers have a backflow preventer as spirally furnished in a meat chopper casing, and are disclosed in the specification of Japanese Patent Application No. 10-228211.

As to the water-swellable crosslinked polymer which is in a hydrogelled state in method (1) above, a hydrogelled crosslinked polymer as obtained by aqueous solution polymerization of an aqueous monomer solution may directly be used, or the dry water-swellable crosslinked polymer may be swollen with water again and then used.

In method (1) above, it is preferable to blend the water-swellable crosslinked polymer of acidity in water and the water-swellable crosslinked polymer of basicity in water under conditions where both polymers are in a hydrogelled state. Or, the water-swellable crosslinked polymer of acidity in water can be dried at high temperature, therefore in view of reducing the drying load and facilitating the particle diameter control (facilitating the pulverization) it is also preferable to blend a dry water-swellable crosslinked polymer of acidity in water and a hydrogelled water-swellable crosslinked polymer of basicity in water.

In method (1) above, in the case where the water-swellable crosslinked polymer of acidity in water is blended in a hydrogelled state, the water-swellable crosslinked polymer of acidity in water is difficult to pulverize after blending, therefore it is desirable to lessen the particle diameter of this polymer before blending, and it is preferable to form this polymer into a hydrogel having an average gel particle diameter of 100 to 1,500 $\mu$m, more preferably 100 to 1,000 $\mu$m, still more preferably 100 to 500 $\mu$m. In the case where the average gel particle diameter is less than 100 $\mu$m, too much force is applied when blending, therefore the particle shapes previous to blending cannot be kept, and the number of effective functional groups in the water-swellable crosslinked polymer of acidity in water and the water-swellable crosslinked polymer of basicity in water is reduced, so it is difficult to exhibit excellent desalting effects. In addition, both water-swellable crosslinked polymers cause the swelling restriction which lowers the saltwater absorption capacity.

In method (1) above, in the case where the water-swellable crosslinked polymer of acidity in water is blended in a dry state, namely, in a state where the water content is in the range of 1 to 20 weight %, it is preferable that this polymer has an average particle diameter of not less than 300 $\mu$m, more preferably of 300 to 1,000 $\mu$m. In the case where the average particle diameter is less than 300 $\mu$m, too much force is applied when blending, therefore the particle shapes previous to blending cannot be kept, and the number of effective functional groups in the water-swellable crosslinked polymer of acidity in water and the water-swellable crosslinked polymer of basicity in water is reduced, so it is difficult to exhibit excellent desalting effects. In addition, both water-swellable crosslinked polymers cause the swelling restriction which lowers the saltwater absorption capacity.

Also in method (1) above, water may be added when blending, and the amount of water as added depends on the crosslinking density of the water-swellable crosslinked polymer of basicity in water and the water-swellable crosslinked polymer of acidity in water, but is preferably in the range of 10~10,000 weight parts, more preferably 50~1,000 weight parts, per 100 weight parts of the water-swellable crosslinked polymers. In the case where the amount of water exceeds 10,000 weight parts, there are disadvantages in that: the strength in a hydrogel state of the water-swellable crosslinked polymer of basicity in water and the water-swellable crosslinked polymer of acidity in water might be low, and the crosslinked structure might be destroyed, and the saltwater absorption speed under a load, the saltwater absorption capacity under a load, and the absorption capacity under a load might therefore be low. On the other hand, in the case where the amount of water is below 10 weight parts, the blending might unfavorably be non-uniform.

In method (2) above, the amount of water as added is preferably not smaller than 5 weight %, more preferably not smaller than 10 weight %, still more preferably not smaller than 15 weight %, of the solid content of the water-swellable crosslinked polymer of acidity in water.

Method (2) above provides the advantage of saving the amount of added water when compared with the amount of water as beforehand contained in the hydrogel in method (1) above. However, method (1) is more preferable in view of the properties of the resultant blend and the strength against mechanical impact.

In methods (1) and (2) above, in the case where the water-swellable crosslinked polymer of acidity in water is blended in a dry state (namely, in a state where the water content is less than 20 weight %), it is preferable to use a water-swellable crosslinked polymer of acidity in water as produced by the following production process, namely, the production process according to the eighth present invention for a water-swellable crosslinked polymer of acidity in water comprising the steps of: carrying out aqueous solution polymerization of a polymerizable monomer in the presence of a copolymerizable crosslinking agent, wherein the polymerizable monomer contains at least one acid group selected from the group consisting of carboxylic acid groups, sulfonic acid groups, and phosphoric acid groups, and 80 to 100 mol % of the acid groups in the polymerizable monomer are present in the acid form; and heating the resultant hydrogelled polymer at a temperature of not lower than 100° C. so that the water content in the polymer will be in the range of 1 to 20 weight % (but not including 20 weight %); and further, if necessary, pulverizing the heated polymer. It is the most important in the eighth present invention that the water content is not less than 1 weight %. If the water content in the water-swellable crosslinked polymer of acidity in water is not less than 1 weight %, this polymer exhibits very high absorption capacity or saltwater absorption capacity when blended with a basic substance (e.g. the water-swellable crosslinked polymer of basicity in water). In comparison, the reduction of the water content to less than 1 weight % immediately deteriorates the absorption capacity or saltwater absorption capacity in the case of blending with the basic substance, thus a discontinuous change is seen with the water content of 1 weight % bordered. It is secondarily important that the heating temperature is not lower than 100° C. The heating temperature lower than 100° C. is inefficient and therefore not fit for industrial practice. The other respects are as stated above.

The partial neutralization and the unification of the water-swellable crosslinked polymer of basicity in water and the water-swellable crosslinked polymer of acidity in water is preferably carried out by blending them without destroying respective crosslinked structures and without lowering the elastic modulus, and it is more preferable that the water-swellable crosslinked polymer of basicity in water and the water-swellable crosslinked polymer of acidity in water are blended such that they can be partially neutralized or be unified in a state of particles in the range of 1~1,000 $\mu$m. In the case where the particle shape of each of the water-swellable crosslinked polymer of basicity in water and the water-swellable crosslinked polymer of acidity in water, resultant from the unification by blending, is smaller than 1 $\mu$m or larger than 1,000 $\mu$m, attention is necessary, because the pulverization yield after drying might be lowered, and because the saltwater absorption speed might be lowered.

For uniformly and surely blending the water-swellable crosslinked polymer of acidity in water and the water-swellable crosslinked polymer of basicity in water to obtain the water-swellable crosslinked polymer compositions according to the third and fourth present inventions, it is preferable to use a blender having a great blending force. Preferable examples of the above blending apparatus include cylinder type blenders, double-wall cone type blenders, V-character-shaped blenders, ribbon type blenders, screw type blenders, fluidized-furnace rotary disk type blenders, gas current type blenders, double-arm type kneaders, internal blenders, pulverizing type kneaders, rotary blenders, screw type push benches, meat choppers containing a back-flow preventer (as, preferably, spirally furnished in a meat chopper casing), and universal blenders. Incidentally, in the present invention, it is preferable to cut both polymers into small particles and preblend them in cut-blending machines, such as speed cutters, crush blenders, and screw type push benches, before blending the polymers.

The water-swellable crosslinked polymer compositions according to the third and fourth present inventions, as obtained in the above way, can be formed into a particulate water-swellable crosslinked polymer composition of the desired particle size, preferably, by being dried and pulverized.

The drying method is carried out in the range of 0~150° C., preferably below 100° C., and can be carried out using conventional dryers or heating-furnaces. Examples of the dryers include decompression dryers, freeze dryers, channel type blending dryers, rotary dryers, disk dryers, fluidized-bed dryers, air blow type dryers, infrared dryers, and heat roll dryers.

In addition, the pulverizing method is not especially limited, either, and conventional apparatuses are available, such as hammer type pulverizers, impact type pulverizers, roll type pulverizers, and jet gas current type pulverizers. However, it is especially preferable to use the roll type pulverizers which rarely divides the bondings between the water-swellable crosslinked polymers.

As to the water-swellable crosslinked polymer compositions according to the third and fourth present inventions, the water content thereof is preferably in the range of 5 to 25 weight %, more preferably 5 to 20 weight %. If the water content of the composition is a high value of not less than 5 weight %, the retainability of bonding by the unification in the third present invention or by the partial neutralization in the fourth present invention is good, so that high saltwater absorption speed or high absorption capacity under a load is exhibited. In the case where the water content is less than 5 weight %, the retainability of bonding is so poor that the bonding moieties are easily broken. In the case where the water content is more than 25 weight %, there are disadvantages in that the whole particles easily aggregate and are therefore difficult to handle, and further in that the absorption capacity under a load is low.

In the water-swellable crosslinked polymer composition, as obtained in the above way, the water-swellable crosslinked polymer of acidity in water and the water-swellable crosslinked polymer of basicity in water are partially neutralized or are unified, so this composition exhibits fast ion-exchanging speed and good desalting efficiency, therefore, has much faster saltwater absorption speed under a load than conventional blends, and further, exhibits excellent absorption capacity under a load.

Especially, the water-swellable crosslinked polymer composition, according to the first present invention, comprises a blend of the water-swellable crosslinked polymer of acidity in water and the water-swellable crosslinked polymer of basicity in water, and is characterized by exhibiting a saltwater absorption capacity of at least 50 g/g under a load of 3.5 g/cm$^2$ in 10 hours, and absorbing 60% of the 10-hour saltwater absorption capacity under the load of 3.5 g/cm$^2$ in less than 5 minutes. The saltwater absorption capacity under a load of 3.5 g/cm$^2$ in 10 hours is preferably not less than 55 g/g, more preferably not less than 60 g/g. Furthermore, the water-swellable crosslinked polymer composition, according to the second present invention, comprises a blend of the water-swellable crosslinked polymer of acidity in water and the water-swellable crosslinked polymer of basicity in water, and is characterized by exhibiting a saltwater absorption capacity of at least 40 g/g under a load of 21 g/cm$^2$ in 10 hours, and absorbing 60% of the 10-hour saltwater absorption capacity under the load of 21 g/cm$^2$ in less than 5 minutes. The saltwater absorption capacity under a load of 21 g/cm$^2$ in 10 hours is preferably not less than 45 g/g, more preferably not less than 50 g/g. Accordingly, the present invention provides the water-swellable crosslinked polymer composition which exhibits equal or higher absorption speed and a remarkably enhanced absorption capacity under a load in comparison with conventional water-absorbent polymers which is neutralized with alkaline-metal salts and of which the surface neighborhood is secondarily crosslinked.

Furthermore, the water-swellable crosslinked polymer composition, according to the fifth present invention, comprises a blend of a water-swellable crosslinked polymer of acidity in water and a water-swellable crosslinked polymer of basicity in water, and is characterized in that the water-swellable crosslinked polymer of acidity in water is a crosslinked polyacrylic acid, and in that the water-swellable crosslinked polymer of basicity in water is a crosslinked polyethylenimine and/or a crosslinked polyallylamine, and further characterized by exhibiting a desalting amount of not less than 0.35 g/g. The desalting amount is preferably not less than 0.38 g/g, and more preferably not less than 0.4 g/g.

In addition, when the water-swellable crosslinked polymer of acidity in water is a polyacrylic acid as obtained by polymerizing a monomer including a major proportion of acrylic acid, great effects are obtainable in that the amount of residual acrylic acid in the water-swellable crosslinked polymer composition can be reduced if a water-swellable crosslinked polymer containing a primary to tertiary amino group which is a water-swellable crosslinked polymer of basicity in water is added to and blended with the water-swellable crosslinked polymer of acidity in water (polyacrylic acid) which is in a hydrogelled state. The amount of residual acrylic acid can be reduced to not more than 100 ppm, and further, can be reduced even to less than 50 ppm (ND).

In addition, in the present invention, if necessary, various functions can be given to the present invention water-swellable crosslinked polymer composition by, in the blending step, further adding other materials, such as disinfectants, deodorants, antimicrobial agents, perfumes, various inorganic powders, foaming agents, pigments, dyes, hydrophilic fibers, fillers, hydrophobic fibers, and manure.

The water-swellable crosslinked polymer composition according to the present invention can particularly fitly be used for various absorbent articles, especially, absorbent structures, which are being thinned more and more, such as disposable diapers, sanitary napkins, and incontinent pads, and further, this composition can provide absorbent articles which can remarkably decrease the leakage to thereby keep their surfaces in a rustling dry state even if used for a long time.

Because the water-swellable crosslinked polymer composition according to the present invention can absorb salt water rapidly, it can favorably be used in the wide range of fields, for example, as follows: sanitary material fields, such as water-absorbing agents for various absorbent articles (e.g. disposable diapers, sanitary napkins, and incontinent pads) and for wipers; food fields, such as freshness-keeping agents and drip-absorbing agents for meat and fish; agricultural and horticultural fields, such as water-holding agents for plants and soil and for tree planting of vertical faces; building material fields, such as paint additives and dewfall preventives; communication fields, such as sealing agents for optical cables and for submarine cables; information fields, such as surface-coating agents for print films; industrial fields, such as solidifying agents for hydrous materials; home use article fields, such as disposable pocket heaters and calcium-chloride-based desiccants; and public works fields, such as sealing agents for public works, and concrete admixtures.

BEST MODE FOR CARRYING OUT THE INVENTION

Figure 1:
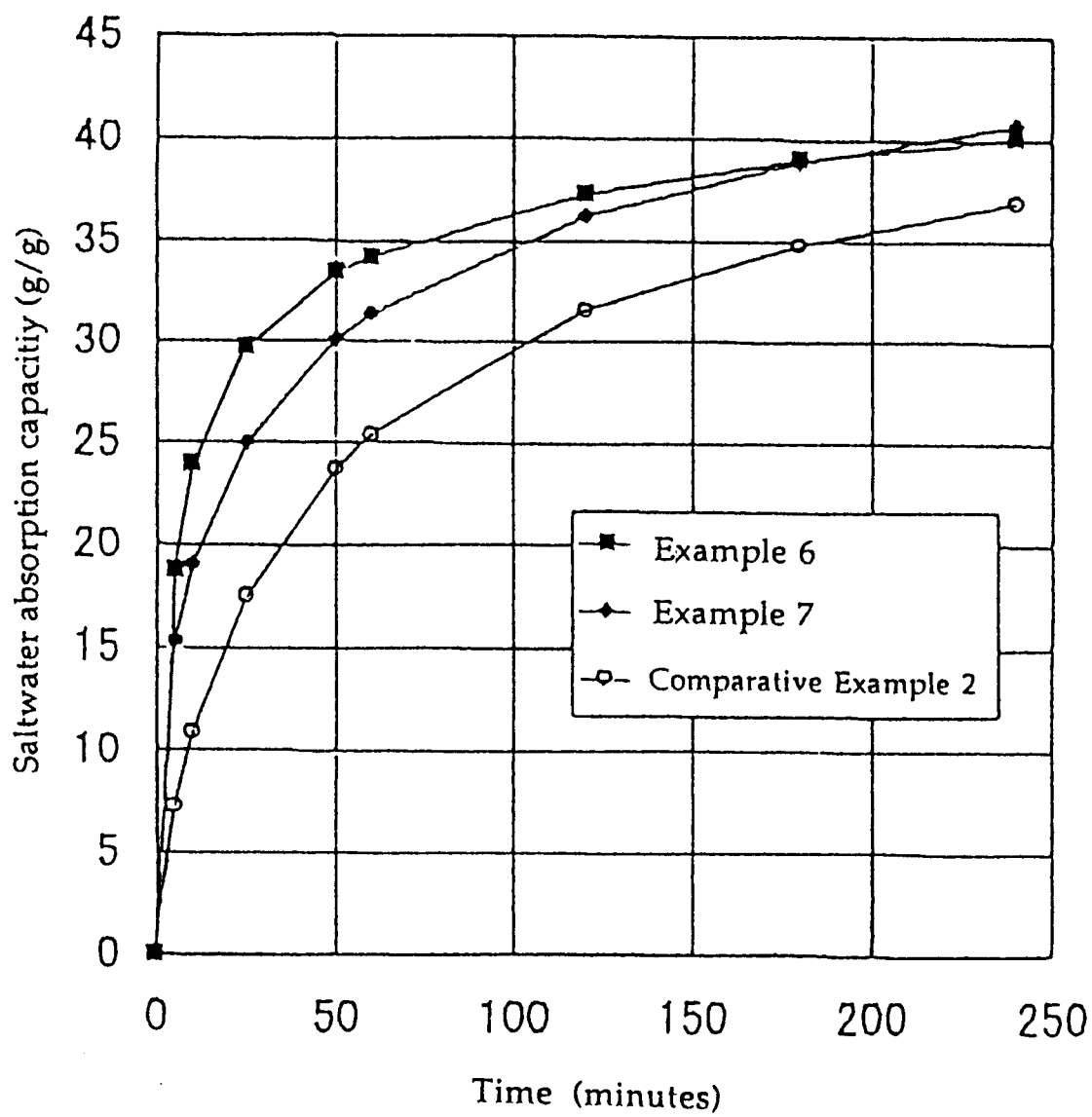
FIG. 1 is a graph of the saltwater absorption capacities of water-swellable crosslinked polymer compositions (6) and (7), according to the present invention, and comparative water-swellable crosslinked polymer composition (2), as plotted at intervals of time.

Hereinafter, the present invention is more specifically illustrated by the following examples of some preferred embodiments in comparison with comparative examples not according to the invention. However, the invention is not limited to these examples. Incidentally, the absorption capacity under a load, the saltwater absorption capacity under a load of 3.5 g/cm$^2$, the saltwater absorption capacity under a load of 21 g/cm$^2$, the saltwater absorption capacity (saltwater absorption capacity under a load of 50 g/cm$^2$), the water content, and the desalting amount of the water-swellable crosslinked polymer composition, and further, the swelling capacity for pure water of the water-swellable crosslinked polymer, the pH of 1% water dispersion of the water-swellable crosslinked polymer, the saltwater absorption speed, the average gel particle diameter of the particulate hydrogelled water-swellable crosslinked polymer, the extractable content in the water-swellable crosslinked polymer, the amount of residual acrylic acid in the water-swellable crosslinked polymer composition were measured by the below-mentioned methods. In addition, unless otherwise noted, the units "part(s)" and "%", as hereinafter simply referred to, denote those by weight.

(a) Absorption Capacity Under Load

First, 0.9 g of water-swellable crosslinked polymer composition was uniformly spread on a stainless wire mesh of 400 mesh (mesh opening size: 38 μm) as attached by fusion to the bottom of a plastic supporting cylinder with an inner diameter of 60 mm. Next, a piston and a load were mounted in sequence on the above water-swellable crosslinked polymer composition, wherein the piston had an outer diameter of only a little smaller than 60 mm and made no gap with the wall face of the supporting cylinder, but was not hindered from moving up and down, and wherein the piston and the load were adjusted such that a load of 50 g/cm$^2$ could uniformly be applied to the water-swellable crosslinked polymer composition. Then, the weight (Wa1) of the resultant set of measurement apparatus was measured.

A glass filter plate of 90 mm in diameter is mounted inside a Petri dish of 150 mm, and a 0.9 wt % aqueous sodium chloride solution (physiological salt solution) is added up to the same level as the surface of the glass filter plate, on which filter paper of 90 mm in diameter is then mounted such that its entire surface will be wetted, and further, an excess of liquid is removed.

The above set of measurement apparatus is mounted on the above wet filter paper, thereby allowing the water-swellable crosslinked polymer composition to absorb the liquid under the load. After the water-absorbent polymer has fallen into a saturated water absorption state (about 20 hours later), the set of measurement apparatus is lifted to measure its weight (Wb1) again. The value, as given by subtracting Wa1 from Wb1, is divided by the weight (0.9 g) of the water-swellable crosslinked polymer composition, thus determining the absorption capacity (g/g) under the load.

Incidentally, the "absorption capacity under a load", as herein simply referred to, is a value as obtained when carrying out the water absorption until the saturated water absorption state is established (about 20 hours later) by the above measurement method. The absorption capacity under a load in each time can be measured by setting the water absorption time to a predetermined time.

(b) Saltwater Absorption Capacity Under Load of 3.5 g/cm$^2$

First, 0.9 g of water-swellable crosslinked polymer composition was uniformly spread on a stainless wire mesh of 400 mesh (mesh opening size: 38 μm) as attached by fusion to the bottom of a plastic supporting cylinder with an inner diameter of 60 mm. Next, a piston and a load were mounted in sequence on the above water-swellable crosslinked polymer composition, wherein the piston had an outer diameter of only a little smaller than 60 mm and made no gap with the wall face of the supporting cylinder, but was not hindered from moving up and down, and wherein the piston and the load were adjusted such that a load of 3.5 g/cm$^2$ could uniformly be applied to the water-swellable crosslinked polymer composition. Then, the weight (Wa2) of the resultant set of measurement apparatus was measured.

A glass filter plate of 90 mm in diameter is mounted inside a Petri dish of 150 mm, and a salt water (1,000 g in total weight as prepared by adding deionized water (solvent) to 2.0 g of potassium chloride, 2.0 g of sodium sulfate, 0.85 g of ammonium dihydrogenphosphate, 0.15 g of diammonium hydrogenphosphate, 0.25 g of calcium chloride dihydrate, and 0.5 g of magnesium chloride hexahydrate) is added up to the same level as the surface of the glass filter plate, on which filter paper of 90 mm in diameter is then mounted such that its entire surface will be wetted, and further, an excess of liquid is removed.

The above set of measurement apparatus is mounted on the above wet filter paper, thereby allowing the water-swellable crosslinked polymer composition to absorb the liquid under the load. After the water-swellable crosslinked polymer composition has absorbed the liquid for 5 minutes, the set of measurement apparatus is lifted to measure its weight (Wb2) again. The value, as given by subtracting Wa2 from Wb2, is divided by the weight (0.9 g) of the water-swellable crosslinked polymer composition, thus determining how large saltwater absorption capacity (g/g) under the load of 3.5 g/cm$^2$ is exhibited in 5 minutes. The above measurement is carried out with the piston and the load still mounted. After the measurement of the weight has ended, the set of measurement apparatus is mounted on the above wet filter paper again, thereby allowing the water-swellable crosslinked polymer composition to absorb the salt water under the load until the next predetermined time (until after 10 hours). Thereafter, the above operation is repeated to determine the saltwater absorption capacity. The value, resultant from the above swelling for 10 hours, was regarded as the saltwater absorption capacity (g/g) under the load of 3.5 g/cm$^2$, and compared with the 5-minute value.

(c) Saltwater Absorption Capacity Under Load of 21 g/cm$^2$

First, 0.9 g of water-swellable crosslinked polymer composition was uniformly spread on a stainless wire mesh of 400 mesh (mesh opening size: 38 μm) as attached by fusion to the bottom of a plastic supporting cylinder with an inner diameter of 60 mm. Next, a piston and a load were mounted in sequence on the above water-swellable crosslinked polymer composition, wherein the piston had an outer diameter of only a little smaller than 60 mm and made no gap with the wall face of the supporting cylinder, but was not hindered from moving up and down, and wherein the piston and the load were adjusted such that a load of 21 g/cm$^2$ could uniformly be applied to the water-swellable crosslinked polymer composition. Then, the weight (Wa3) of the resultant set of measurement apparatus was measured.

A glass filter plate of 90 mm in diameter is mounted inside a Petri dish of 150 mm, and a salt water (1,000 g in total weight as prepared by adding deionized water (solvent) to 2.0 g of potassium chloride, 2.0 g of sodium sulfate, 0.85 g of ammonium dihydrogenphosphate, 0.15 g of diammonium hydrogenphosphate, 0.25 g of calcium chloride dihydrate, and 0.5 g of magnesium chloride hexahydrate) is added up to the same level as the surface of the glass filter plate, on which filter paper of 90 mm in diameter is then mounted such that its entire surface will be wetted, and further, an excess of liquid is removed.

The above set of measurement apparatus is mounted on the above wet filter paper, thereby allowing the water-swellable crosslinked polymer composition to absorb the liquid under the load. After the water-swellable crosslinked polymer composition has absorbed the liquid for 5 minutes, the set of measurement apparatus is lifted to measure its weight (Wb3) again. The value, as given by subtracting Wa3 from Wb3, is divided by the weight (0.9 g) of the water-swellable crosslinked polymer composition, thus determining how large saltwater absorption capacity (g/g) under the load of 21 g/cm$^2$ is exhibited in 5 minutes. The above measurement is carried out with the piston and the load still mounted. After the measurement of the weight has ended, the set of measurement apparatus is mounted on the above wet filter paper again, thereby allowing the water-swellable crosslinked polymer composition to absorb the salt water under the load until the next predetermined time (until after 10 hours). Thereafter, the above operation is repeated to determine the saltwater absorption capacity. The value, resultant from the above swelling for 10 hours, was regarded as the saltwater absorption capacity (g/g) under the load of 21 g/cm², and compared with the 5-minute value.

(d) Saltwater Absorption Capacity (Saltwater Absorption Capacity Under a Load of 50 g/cm²)

First, 0.9 g of water-swellable crosslinked polymer composition was uniformly spread on a stainless wire mesh of 400 mesh (mesh opening size: 38 μm) as attached by fusion to the bottom of a plastic supporting cylinder with an inner diameter of 60 mm. Next, a piston and a load were mounted in sequence on the above water-swellable crosslinked polymer composition, wherein the piston had an outer diameter of only a little smaller than 60 mm and made no gap with the wall face of the supporting cylinder, but was not hindered from moving up and down, and wherein the piston and the load were adjusted such that a load of 50 g/cm² could uniformly be applied to the water-swellable crosslinked polymer composition. Then, the weight (Wa4) of the resultant set of measurement apparatus was measured.

A glass filter plate of 90 mm in diameter is mounted inside a Petri dish of 150 mm, and a salt water (1,000 g in total weight as prepared by adding deionized water (solvent) to 2.0 g of potassium chloride, 2.0 g of sodium sulfate, 0.85 g of ammonium dihydrogenphosphate, 0.15 g of diammonium hydrogenphosphate, 0.25 g of calcium chloride dihydrate, and 0.5 g of magnesium chloride hexahydrate) is added up to the same level as the surface of the glass filter plate, on which filter paper of 90 mm in diameter is then mounted such that its entire surface will be wetted, and further, an excess of liquid is removed.

The above set of measurement apparatus is mounted on the above wet filter paper, thereby allowing the water-swellable crosslinked polymer composition to absorb the liquid under the load. After the water-swellable crosslinked polymer composition has absorbed the liquid for a predetermined time, the set of measurement apparatus is lifted to measure its weight (Wb4) again. The value, as given by subtracting Wa4 from Wb4, is divided by the weight (0.9 g) of the water-swellable crosslinked polymer composition, thus determining the saltwater absorption capacity (g/g). The above measurement is carried out with the piston and the load still mounted. After the measurement of the weight has ended, the set of measurement apparatus is mounted on the above wet filter paper again, thereby allowing the water-swellable crosslinked polymer composition to absorb the salt water under the load until the next predetermined time. Thereafter, the above operation is repeated to compare the saltwater absorption speed. The larger the saltwater absorption capacity as exhibited in the initial stage is, the faster the saltwater absorption speed under a heavy load is.

(e) Water Content

The initial weight (Wa5) of the water-swellable crosslinked polymer composition is beforehand measured, and then the weight (Wb5) is measured after drying in a hot-air dryer of 105° C. for 3 hours. The value, as given by subtracting Wb5 from Wa5, is divided by Wa5, and the resultant divided value is represented by the percentage, which is regarded as the water content (%) of the water-swellable crosslinked polymer composition.

(f) Desalting Amount

First, 1.0 g of water-swellable crosslinked polymer composition is placed into 100 g of physiological salt solution (0.9 wt % aqueous sodium chloride solution) in a beaker of 200 ml and then gently stirred, thereby being swollen. After swelling for 4 hours, the liquid containing the swollen gel is filtered by suction, and the amount (g/g) of desalting by the gel is determined from amount W1 (g) of the separated filtrate and from sodium chloride concentration C1 (wt %) as determined from the electric conductivity of the filtrate.

$$\text{Desalting amount (g/g)} = 0.9 - W1 \times C1/100$$

(g) Swelling Capacity for Pure Water of Water-swellable Crosslinked Polymer and pH of 1% Water Dispersion Thereof First, 0.2 g of water-swellable crosslinked polymer was uniformly put into a nonwoven fabric bag (60 mm×60 mm) and then immersed into 20 g of distilled water. After 60 minutes, the bag was drawn up and then drained with a centrifuge at 250 G for 3 minutes to measure the weight W1 (g) of the bag. In addition, the same operation was carried out without the water-swellable crosslinked polymer, and the resultant weight W0 (g) was measured. Then, the value, as given by subtracting W0 from W1, was divided by the weight (g) of the water-swellable crosslinked polymer, thus determining the swelling capacity (g/g) for pure water of the water-swellable crosslinked polymer. On the other hand, the pH of the distilled water, as left behind by the drawing up of the bag, was measured with a pH meter and regarded as the pH of the 1% water dispersion of the polymer.

(h) Saltwater Absorption Speed

First, 1.0 g of water-swellable crosslinked polymer composition was uniformly spread into a Petri dish of 58 mm in inner diameter and 12 mm in depth. Thereafter, 20 g of a salt water (1,000 g in total weight as prepared by adding deionized water (solvent) to 2.0 g of potassium chloride, 2.0 g of sodium sulfate, 0.85 g of ammonium dihydrogenphosphate, 0.15 g of diammonium hydrogenphosphate, 0.25 g of calcium chloride dihydrate, and 0.5 g of magnesium chloride hexahydrate) was poured all at once and gently onto a central portion of the Petri dish. Then, the period of time, starting when the salt water was poured and ending when it was confirmed with the eye that the salt water had entirely been absorbed by the water-swellable crosslinked polymer composition, was measured and regarded as the saltwater absorption speed (seconds).

(i) Average Gel Particle Diameter of Particulate Hydrogelled Water-swellable Crosslinked Polymer A sample of 30 g of particulate hydrogelled water-swellable crosslinked polymer (solid content: α wt %) was placed into 1,000 g of 3 wt % aqueous sodium chloride solution, and they were stirred for 180 minutes with a stirrer chip at 300 rpm, whereby a dispersion was obtained. After stirring, the above dispersion was placed onto sieves (mesh opening sizes: 4.0 mm, 2.0 mm, 1.2 mm, 0.60 mm, 0.30 mm, 0.15 mm, 0.075 mm), and then the filtrate as passed through the sieves were re-poured onto the sieves repeatedly, thus classifying the hydrogelled water-swellable crosslinked polymer. The classified fractions of the hydrogelled water-swellable crosslinked polymer on the respective sieves were sufficiently drained and then weighed. The sieve mesh opening size was calculated in terms of sieve mesh opening size $R(\alpha)$ corresponding to solid content α wt % of the hydrogelled water-swellable crosslinked polymer in accordance with the below-mentioned equation. The particle diameter distribution of the particulate hydrogelled water-swellable crosslinked polymer corresponding to solid content α wt % was plotted on logarithmic probability paper. The particle diameter corresponding to 50 wt % that was the integrated percentage of the resultant plot on the sieves was regarded as the average particle diameter of the sample.

$$R(\alpha)(\text{mm}) = \sqrt[3]{30(g)/w(g)} \times \gamma(\text{mm}) \quad \text{[Equation 1]}$$

$R(\alpha)$: Mesh opening size (mm) of a sieve as calculated in terms of the hydrogelled water-swellable crosslinked polymer with a solid content of $\alpha$ wt %.

w: Total weight (g) of the hydrogelled water-swellable crosslinked polymer after being classified and drained.

$\gamma$: Mesh opening size (mm) of a sieve onto which the hydrogelled water-swellable crosslinked polymer as swollen in the 3 wt % aqueous sodium chloride solution was classified.

(j) Extractable Content in Water-swellable Crosslinked Polymer of Acidity in Water A gel of water-swellable crosslinked polymer of acidity in water, of which the amount (Wa [g]) corresponded to 1 g in terms of solid content, was swollen under stirring in 184.3 g of 0.9% salt solution (physiological salt solution) for 16 hours. After 16 hours, the swollen gel was filtered off with filter paper (Toyo Filter Paper No. 2), and the resultant filtrate was pH-titrated to determine the amount (g) of extractable components, as contained in the filtrate, of the water-swellable crosslinked polymer of acidity in water. The value, as given by dividing the above-determined amount of the polymer in the filtrate by 1 g, was regarded as the extractable content (%) of the water-swellable crosslinked polymer of acidity in water.

(k) Extractable Content in Water-swellable Crosslinked Polymer of Basicity in Water A gel of water-swellable crosslinked polymer of basicity in water, of which the amount (Wa [g]) corresponded to 1 g in terms of solid content, was weighed out with the accuracy of 0.0001 g, and then added into 200 g of pure water, and then stirred for 16 hours. The resultant mixed solution was filtered with filter paper (No. 2 made by ADVANTEC Corporation), and the filtrate was separated. The amount (Wb [g]) corresponding to 1~3 mg of dissolved amine component was sampled from the filtrate into a beaker of 200 ml, and then pure water was added thereto to increase the entirety to 50 g, and further, 0.1 N hydrochloric acid was then added thereto to adjust pH to 1~2. A few drops of Toluidine Blue was added to the resultant solution, and then a 1/400 N potassium polyvinyl sulfate solution (PVSK, for colloidal titration) was further dropped, when the point at which the color of the solution had changed from blue to reddish violet was regarded as the end point (T [ml]). The extractable content of the water-swellable crosslinked polymer of basicity in water was calculated from the following equation:

$$\text{Extractable content of water-swellable crosslinked polymer of basicity in water (\%)} = \frac{T \cdot 1/400 \cdot F \cdot M \cdot \{200 + Wa(1 - S/100)\}}{1000 \cdot Wb \cdot Wa \cdot S/100} \quad \text{[Equation 2]}$$

F: Titer of PVSK

M: Molecular weight of repeating unit

S: Solid content of gel (wt %)

(1) Amount of Residual Acrylic Acid in Water-swellable Crosslinked Polymer Composition Half one weight part of water-swellable crosslinked polymer composition was placed into 1,000 weight parts of pure water, and they were stirred. After 16 hours, the resultant extractive was measured by liquid chromatography, and the resultant value was calculated in terms of the charged water-swellable crosslinked polymer composition.

REFERENTIAL EXAMPLE 1

First, 68.97 parts of acrylic acid, 0.74 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 4.5 minutes, a polymerization reaction got started, and after 21 minutes, the reaction system reached the peak temperature. Thirty minutes after the polymerization temperature reached its peak, the resultant hydrogelled crosslinked polymer was got out and regarded as water-swellable crosslinked polymer (1) of acidity in water, which polymer had an extractable content of 2.5%, and absorbed 9.4 g/g of pure water to swell therewith per gram of the solid content of the polymer. In addition, the pH of the 1% water dispersion of the polymer was 4.98.

REFERENTIAL EXAMPLE 2

First, 69.63 parts of acrylic acid, 0.074 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 21° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 3 minutes, a polymerization reaction got started, and after 32 minutes, the reaction system reached the peak temperature. Thirty minutes after the polymerization temperature reached its peak, the resultant hydrogelled crosslinked polymer was got out and regarded as water-swellable crosslinked polymer (2) of acidity in water, which polymer had an extractable content of 8.5%, and absorbed 28.6 g/g of pure water to swell therewith per gram of the solid content of the polymer. In addition, the pH of the 1% water dispersion of the polymer was 5.04.

REFERENTIAL EXAMPLE 3

First, 69.33 parts of acrylic acid, 0.37 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 21° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 3 minutes, a polymerization reaction got started, and after 32 minutes, the reaction system reached the peak temperature. Thirty minutes after the polymerization temperature reached its peak, the resultant hydrogelled crosslinked polymer was got out and regarded as water-swellable crosslinked polymer (3) of acidity in water, which polymer had an extractable content of 2.7%, and absorbed 12.3 g/g of pure water to swell therewith per gram of the solid content of the polymer. In addition, the pH of the 1% water dispersion of the polymer was 5.07.

REFERENTIAL EXAMPLE 4

First, 10 liters of cyclohexane solution, containing 100 g of inorganic particles (trade name: Aerosil R972, made by Nippon Aerosil Co., Ltd.), was placed into a stainless bottle of 20 liters with a dropping funnel, a stirrer, a thermometer, and a reflux condenser, and then stirred at room temperature. Next, 363 g of 50% aqueous solution of ethylene glycol diglycidyl ether (trade name: Denacol EX810, made by Nagase Chemicals, Ltd.) (crosslinking agent) was added under stirring to an aqueous polyethylenimine solution having been cooled to 0° C. beforehand and comprising 5,636 g of 30% polyethylenimine (trade name: Epomin P-1000, made by Nippon Shokubai Co., Ltd.) and 4,000 g of pure water, thus preparing an aqueous solution containing a crosslinking agent and a hydrophilic high-molecular compound. Then, this solution was added to the above cyclohexane solution at room temperature under stirring. Under stirring, the temperature of the system was gradually raised to 65° C., and the reaction was carried out at 65 ° C. for 3 hours. Then, the temperature of the system was cooled to room temperature, and the resultant spherical hydrogel was filtrated by suction and then dried under decompression at 60° C. for 48 hours, thus obtaining water-swellable crosslinked polymer (1) of basicity in water, which had a water content of 15%, and was rustling, and contained an amino group. The resultant water-swellable crosslinked polymer (1) of basicity in water had an average particle diameter of 420 μm and an extractable content of 7%, and absorbed 9.3 g/g of pure water to swell therewith per gram of the solid content of the polymer. In addition, the pH of the 1% water dispersion of the polymer was 9.77.

EXAMPLE 1

First, 100 parts of water-swellable crosslinked polymer (1) of acidity in water, as obtained in Referential Example 1, and 12.1 parts of water-swellable crosslinked polymer (1) of basicity in water, as obtained in Referential Example 4, were blended by being stirred in a kneader under conditions where the facial pressure due to blending was less than 1 kg/cm², thus obtaining a blended and unified product of both polymers. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (1) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The absorption capacity under a load of water-swellable crosslinked polymer composition (1) according to the present invention was 25.4 g/g.

EXAMPLE 2

Water-swellable crosslinked polymer composition (2) according to the present invention was obtained in the same way as of Example 1 except that water-swellable crosslinked polymer (1) of acidity in water of Example 1 was replaced with water-swellable crosslinked polymer (2) of acidity in water as obtained in Referential Example 2. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. The absorption capacity under a load of water-swellable crosslinked polymer composition (2) according to the present invention was 32.1 g/g.

EXAMPLE 3

Water-swellable crosslinked polymer composition (3) according to the present invention was obtained in the same way as of Example 1 except that water-swellable crosslinked polymer (1) of acidity in water of Example 1 was replaced with water-swellable crosslinked polymer (3) of acidity in water as obtained in Referential Example 3. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. The absorption capacity under a load of water-swellable crosslinked polymer composition (3) according to the present invention was 30.0 g/g.

EXAMPLE 4

First, 100 parts of water-swellable crosslinked polymer (1) of acidity in water, as obtained in Referential Example 1, and 9.2 parts of water-swellable crosslinked polymer (1) of basicity in water, as obtained in Referential Example 4, were blended in a kneader under stirring, thus obtaining a blended and unified product of both polymers. This blend was dried in a hot-air drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (4) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The absorption capacity under a load of water-swellable crosslinked polymer composition (4) according to the present invention was 25.2 g/g.

EXAMPLE 5

First, 100 parts of water-swellable crosslinked polymer (1) of acidity in water, as obtained in Referential Example 1; and 12 parts of water-swellable crosslinked polymer (1) of basicity in water, as obtained in Referential Example 4, were blended in a kneader under stirring, thus obtaining a blended and unified product of both polymers. This blend was dried in a hot-air drier of 60° C., and then pulverized with a laboratory pulverizer. The resultant pulverized product was sieved with a wire mesh of 850 μm in mesh opening size to separate what passed through it, thus obtaining water-swellable crosslinked polymer composition (5) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The absorption capacity under a load of water-swellable crosslinked polymer composition (5) according to the present invention was 27.5 g/g.

COMPARATIVE EXAMPLE 1

First, 100 parts of water-swellable crosslinked polymer (1) of acidity in water, as obtained in Referential Example 1, and 22 parts of sodium carbonate powder (special grade reagent) were blended in a kneader under stirring, and then 100 parts of water was added to continue the blending, thus obtaining a blend of both materials. This blend was left at room temperature for 3 days, and then dried in a hot-air drier of 160° C., and then pulverized with a laboratory pulverizer. The resultant pulverized product was sieved with a wire mesh of 850 μm in mesh opening size to separate what passed through it, thus obtaining comparative water-swellable crosslinked polymer composition (1), of which the absorption capacity under a load was 9.6 g/g.

REFERENTIAL EXAMPLE 5

First, 69.11 parts of acrylic acid, 0.59 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 6 minutes, a polymerization reaction got started, and after 32 minutes, the reaction system reached the peak temperature. Thirty minutes after the polymerization temperature reached its peak, the resultant hydrogelled crosslinked polymer was got out, thus obtaining hydrogelled water-swellable crosslinked polymer (4) of acidity in water, which polymer had an extractable content of 2.7%, and absorbed 10.2 g/g of pure water to swell therewith per gram of the solid content of the polymer. In addition, the pH of the 1% water dispersion of the polymer was 5.00.

REFERENTIAL EXAMPLE 6

First, 69.26 parts of acrylic acid, 0.44 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 3 minutes, a polymerization reaction got started, and after 25 minutes, the reaction system reached the peak temperature. Thirty minutes after the polymerization temperature reached its peak, the resultant hydrogelled crosslinked polymer was got out, thus obtaining hydrogelled water-swellable crosslinked polymer (5) of acidity in water, which polymer had an extractable content of 2.7%, and absorbed 11.8 g/g of pure water to swell therewith per gram of the solid content of the polymer. In addition, the pH of the 1% water dispersion of the polymer was 4.91.

REFERENTIAL EXAMPLE 7

First, 10 liters of cyclohexane solution, containing 100 g of inorganic particles (trade name: Aerosil R972, made by Nippon Aerosil Co., Ltd.), was placed into a stainless bottle of 20 liters with a dropping funnel, a stirrer, a thermometer, and a reflux condenser, and then stirred at room temperature. Next, 363 g of 50% aqueous solution of ethylene glycol diglycidyl ether (trade name: Denacol EX810, made by Nagase Chemicals, Ltd.) (crosslinking agent) was added under stirring to an aqueous polyethylenimine solution having been cooled to 0° C. beforehand and comprising 5,636 g of 30% polyethylenimine (trade name: Epomin P-1000, made by Nippon Shokubai Co., Ltd.) and 4,000 g of pure water, thus preparing an aqueous solution containing a crosslinking agent and a hydrophilic high-molecular compound. Then, this solution was added to the above cyclohexane solution at room temperature under stirring. Under stirring, the temperature of the system was gradually raised to 65° C., and the reaction was carried out at 65° C. for 3 hours. Then, the temperature of the system was cooled to room temperature, and the resultant spherical hydrogel was filtrated by suction, and then immersed in a large amount of pure water for 24 hours, and then filtrated, and then dried under decompression at 60° C. for 60 hours, thus obtaining water-swellable crosslinked polymer (2) of basicity in water, which polymer had an extractable content of 0.3%, an average particle diameter of 450 μm, and a water content of 12%, and absorbed 10.1 g/g of pure water to swell therewith per gram of the solid content of the polymer. In addition, the pH of the 1% water dispersion of the polymer was 10.11.

REFERENTIAL EXAMPLE 8

First, 68.97 parts of acrylic acid, 0.74 parts of N,N'-methylenebisacrylamide (copolymerizable crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 4.5 minutes, a polymerization reaction got started, and after 21 minutes, the reaction system reached the peak temperature. Thirty minutes after the polymerization temperature reached its peak, the resultant hydrogelled crosslinked polymer was got out and then dried at 60° C. for 24 hours. The resultant dried product was pulverized with a laboratory pulverizer, and the resultant pulverized product was sieved with a wire mesh of 850 $\mu$m in mesh opening size to separate what passed through it, thus obtaining water-swellable crosslinked polymer (6) of acidity in water, which polymer absorbed 9.3 g/g of pure water to swell therewith. In addition, the pH of the 1% water dispersion of the polymer was 4.99.

REFERENTIAL EXAMPLE 9

First, 20 parts of 10% aqueous polyallylamine solution (trade name: PAA-10C, made by Nitto Boseki Co., Ltd.) was mixed with 0.5 parts of ethylene glycol diglycidyl ether (trade name: Denacol EX810, made by Nagase Chemicals, Ltd.) (crosslinking agent), and the resultant mixture was heated in an airtight vessel at 50° C. for 24 hours, thus obtaining a crosslinked polyallylamine. The resultant crosslinked polyallylamine was cut into small pieces in a mixer, and then immersed in a large quantity of pure water for 24 hours, and then filtrated, thus obtaining hydrogelled water-swellable crosslinked polymer (3) of basicity in water, which polymer absorbed 10.2 g/g of pure water to swell therewith per gram of the solid content of the polymer. In addition, the extractable content of the polymer was 0.2%, and the pH of the 1% water dispersion of the polymer was 8.44.

REFERENTIAL EXAMPLE 10

First, 20 parts of 10% aqueous polyallylamine solution (trade name: PAA-10C, made by Nitto Boseki Co., Ltd.) was mixed with 0.5 parts of ethylene glycol diglycidyl ether (trade name: Denacol EX810, made by Nagase Chemicals, Ltd.) (crosslinking agent), and the resultant mixture was heated in an airtight vessel at 60° C. for 3 hours, whereby a hydrogelled crosslinked polyallylamine was obtained and regarded as hydrogelled water-swellable crosslinked polymer (4) of basicity in water, which polymer absorbed 10.0 g/g of pure water to swell therewith per gram of the solid content of the polymer. In addition, the pH of the 1% water dispersion of the polymer was 8.50, and the extractable content of the polymer was 3.2%.

EXAMPLE 6

First, 100 parts of hydrogelled water-swellable crosslinked polymer (1) of acidity in water, as obtained in Referential Example 1, and 20 parts of water-swellable crosslinked polymer (2) of basicity in water, as obtained in Referential Example 7, were blended while being cut into small pieces in a blender, and the resultant blend was caused to pass through a meat chopper (this was a meat chopper which had a backflow preventer as spirally furnished in a meat chopper casing, and all the meat choppers as used in the below-mentioned Examples were meat choppers which similarly had a backflow preventer as spirally furnished in a meat chopper casing), thus obtaining a blended and unified product, when the facial pressure was 1 kg/cm$^2$. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 $\mu$m in mesh opening size to separate what passed through it, thus obtaining water-swellable crosslinked polymer composition (6) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited saltwater absorption capacities of 23.9 g/g in 10 minutes and 34.2 g/g in 60 minutes after starting to absorb the liquid.

COMPARATIVE EXAMPLE 2

One hundred parts of water-swellable crosslinked polymer (6) of acidity in water, as obtained in Referential Example 8, and 100 parts of water-swellable crosslinked polymer (2) of basicity in water, as obtained in Referential Example 7, were blended under dry conditions, thus obtaining comparative water-swellable crosslinked polymer composition (2), which exhibited saltwater absorption capacities of 10.9 g/g in 10 minutes and 25.4 g/g in 60 minutes after starting to absorb the liquid. As is evident from this result, a water-swellable crosslinked polymer composition in which the water-swellable crosslinked polymer of acidity in water and the water-swellable crosslinked polymer of basicity in water are not unified with each other would not exhibit sufficient saltwater absorption speed even if the compositions and the ratios of both polymers in such a water-swellable crosslinked polymer composition were the same as those in a water-swellable crosslinked polymer composition in which both polymers are unified with each other.

COMPARATIVE EXAMPLE 3

Water-swellable crosslinked polymer of basicity in water was synthesized according to the synthesizing method for sample 14 as set forth in WO 98/24832. Then, 100 parts of water-swellable crosslinked polymer (6) of acidity in water, as obtained in Referential Example 8, and 100 parts of the above water-swellable crosslinked polymer of basicity in water were blended under dry conditions, thus obtaining comparative water-swellable crosslinked polymer composition (3), which merely exhibited saltwater absorption capacities (under a load of 50 g/cm$^2$) of 3.7 g/g in 10 minutes and 9.1 g/g in 60 minutes, and further, only 17.1 g/g even in 6 hours, after starting to absorb the liquid.

EXAMPLE 7

First, 100 parts of hydrogelled water-swellable crosslinked polymer (4) of acidity in water, as obtained in Referential Example 5, and 20 parts of water-swellable crosslinked polymer (2) of basicity in water, as obtained in Referential Example 7, were blended while being cut into small pieces in a blender, and the resultant blend was caused to pass through a meat chopper such that the facial pressure due to blending would be 1.5 kg/cm$^2$, thus obtaining a blended and unified product. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved to separate fractions between wire meshes of 500~150 μm in mesh opening size, thus obtaining water-swellable crosslinked polymer composition (7) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited saltwater absorption capacities of 19.0 g/g in 10 minutes and 31.4 g/g in 60 minutes after starting to absorb the liquid. FIG. 1 shows results of comparing the saltwater absorption speeds of water-swellable crosslinked polymer compositions (6) and (7), according to the present invention, and comparative water-swellable crosslinked polymer composition (2).

EXAMPLE 8

First, 100 parts of hydrogelled water-swellable crosslinked polymer (5) of acidity in water, as obtained in Referential Example 6, and 20 parts of water-swellable crosslinked polymer (2) of basicity in water, as obtained in Referential Example 7, and further, 160 parts of pure water were blended while being cut into small pieces in a blender, and the resultant blend was caused to pass through a meat chopper, thus obtaining a blended and unified product. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 500 μm in mesh opening size to separate what passed through it, thus obtaining water-swellable crosslinked polymer composition (8) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited saltwater absorption capacities of 26.6 g/g in 10 minutes and 32.0 g/g in 60 minutes after starting to absorb the liquid.

EXAMPLE 9

First, 100 parts of hydrogelled water-swellable crosslinked polymer (1) of acidity in water, as obtained in Referential Example 1, and 20 parts of water-swellable crosslinked polymer (2) of basicity in water, as obtained in Referential Example 7, were blended while being cut into small pieces in a blender, and the resultant blend was caused to pass through a meat chopper, thus obtaining a blended and unified product. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 500 μm in mesh opening size to separate what passed through it, thus obtaining water-swellable crosslinked polymer composition (9) according to the present invention, in which the water-swellable crosslinked polymer of basicity in water and the water- swellable crosslinked polymer of acidity in water were unified with each other, and in which part of acid groups of the water-swellable crosslinked polymer of acidity in water were neutralized with the water-swellable crosslinked polymer of basicity in water. This composition exhibited saltwater absorption capacities of 26.2 g/g in 10 minutes and 31.7 g/g in 60 minutes after starting to absorb the liquid.

EXAMPLE 10

One hundred and forty-five parts of hydrogelled water-swellable crosslinked polymer (3) of basicity in water, as obtained in Referential Example 9, was added to 100 parts of hydrogelled water-swellable crosslinked polymer (4) of acidity in water, as obtained in Referential Example 5, and they were blended while being cut into small pieces in a blender, and the resultant blend was caused to pass through a meat chopper, thus obtaining a blended and unified product. This blend was dried in a decompression drier of 60° C., and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (10) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited saltwater absorption capacities of 27.5 g/g in 10 minutes and 40.4 g/g in 60 minutes after starting to absorb the liquid.

EXAMPLE 11

First, 100 parts of hydrogelled water-swellable crosslinked polymer (1) of acidity in water, as obtained in Referential Example 1, and 20 parts of water-swellable crosslinked polymer (2) of basicity in water, as obtained in Referential Example 7, were blended while being crushed in a kneader, and the resultant blend was caused to pass through a meat chopper, thus obtaining a blended and unified product. This blend was dried in a hot-air drier of 60° C. for 2 hours, and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (11) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition had a water content of 8.4 %, and exhibited the following saltwater absorption capacities: under a load of 3.5 g/cm$^2$, 54.1 g/g in 10 hours and 37.9 g/g in 5 minutes; under a load of 21 g/cm$^2$, 46.5 g/g in 10 hours and 29.0 g/g in 5 minutes; and, under a load of 50 g/cm$^2$, 34.2 g/g in 1 hours and 40.0 g/g in 4 hours.

EXAMPLE 12

One hundred and forty-five parts of hydrogelled water-swellable crosslinked polymer (4) of basicity in water, as obtained in Referential Example 10, was added to 100 parts of hydrogelled water-swellable crosslinked polymer (4) of acidity in water, as obtained in Referential Example 5, and they were blended while being crushed in a kneader, and the resultant blend was caused to pass through a meat chopper, thus obtaining a blended and unified product. This blend was dried in a hot-air drier of 60° C. for 2 hours, and 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (12) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition had a water content of 7.5 %, and exhibited the following saltwater absorption capacities: under a load of 3.5 g/cm$^2$, 60.7 g/g in 10 hours and 40.7 g/g in 5 minutes; under a load of 21 g/cm$^2$, 54.3 g/g in 10 hours and 35.2 g/g in 5 minutes; and, under a load of 50 g/cm$^2$, 44.5 g/g in 1 hours and 50.0 g/g in 4 hours; and further, exhibited a desalting amount of 0.43 g/g.

REFERENTIAL EXAMPLE 11

Hydrogelled water-swellable crosslinked polymer (4) of acidity in water, as obtained in Referential Example 5, was cut with a meat chopper as furnished with a plate having apertures of 9.5 mm, thus obtaining acid particulate gel (1) with an average gel particle diameter of 1,000 μm.

REFERENTIAL EXAMPLE 12

Hydrogelled water-swellable crosslinked polymer (4) of acidity in water, as obtained in Referential Example 5, was cut with a meat chopper as furnished with a plate of 6.0 mm in aperture, thus obtaining acid particulate gel (2) with an average gel particle diameter of 650 μm.

REFERENTIAL EXAMPLE 13

Hydrogelled water-swellable crosslinked polymer (4) of acidity in water, as obtained in Referential Example 5, was cut with a meat chopper as furnished with a plate of 4.5 mm in aperture, thus obtaining acid particulate gel (3) with an average gel particle diameter of 340 μm.

REFERENTIAL EXAMPLE 14

Hydrogelled water-swellable crosslinked polymer (4) of basicity in water, as obtained in Referential Example 10, was cut with a meat chopper as furnished with a plate of 4.5 mm in aperture, thus obtaining basic particulate gel (1) with an average gel particle diameter of 200 μm.

EXAMPLE 13

One hundred and forty-five parts of basic particulate gel (1) of basicity in water, as obtained in Referential Example 14, and 100 parts of acid particulate gel (1) of acidity in water, as obtained in Referential Example 11, were blended in a kneader, and the resultant blend was caused to pass through a meat chopper, thus obtaining a blended and unified product. This blend was dried in a hot-air drier of 60° C. for 1 hour, and then pulverized with a laboratory pulverizer as equipped with a screen having apertures of 2 mm, thus obtaining water-swellable crosslinked polymer composition (13) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited a saltwater absorption capacity of 41.3 g/g in 1 hour (under a load of 50 g/cm$^2$) and a saltwater absorption capacity of 46.3 g/g in 4 hours (under a load of 50 g/cm$^2$).

EXAMPLE 14

Water-swellable crosslinked polymer composition (14) according to the present invention was obtained in the same way as of Example 13 except that the acid particulate gel of acidity in water was changed to acid particulate gel (2) as obtained in Referential Example 12. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 43.3 g/g in 1 hour (under a load of 50 g/cm$^2$) and a saltwater absorption capacity of 48.5 g/g in 4 hours (under a load of 50 g/cm$^2$).

EXAMPLE 15

Water-swellable crosslinked polymer composition (15) according to the present invention was obtained in the same way as of Example 13 except that the acid particulate gel of acidity in water was changed to acid particulate gel (3) as obtained in Referential Example 13. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 40.8 g/g in 1 hour (under a load of 50 g/cm$^2$) and a saltwater absorption capacity of 49.6 g/g in 4 hours (under a load of 50 g/cm$^2$).

EXAMPLE 16

One hundred and forty-five parts of basic particulate gel (1) of basicity in water, as obtained in Referential Example 14, and 100 parts of acid particulate gel (1) of acidity in water, as obtained in Referential Example 11, were blended in a kneader, and the resultant blend was caused to pass through a meat chopper, thus obtaining a blended and unified product. This blend was dried in a hot-air drier of 60° C. for 1 hour, and then caused to twice pass through a laboratory pulverizer as equipped with a screen having apertures of 2 mm, thus obtaining water-swellable swellable crosslinked polymer composition (16) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition exhibited a saltwater absorption capacity of 43.5 g/g in 1 hour (under a load of 50 g/cm$^2$) and a saltwater absorption capacity of 48.3 g/g in 4 hours (under a load of 50 g/cm$^2$).

EXAMPLE 17

Water-swellable crosslinked polymer composition (17) according to the present invention was obtained in the same way as of Example 16 except that the acid particulate gel of acidity in water was changed to acid particulate gel (2) as obtained in Referential Example 12. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 44.9 g/g in 1 hour (under a load of 50 g/cm$^2$) and a saltwater absorption capacity of 49.5 g/g in 4 hours (under a load of 50 g/cm$^2$).

EXAMPLE 18

Water-swellable crosslinked polymer composition (18) according to the present invention was obtained in the same way as of Example 16 except that the acid particulate gel of acidity in water was changed to acid particulate gel (3) as obtained in Referential Example 13. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 39.3 g/g in 1 hour (under a load of 50 g/cm$^2$) and a saltwater absorption capacity of 51.1 g/g in 4 hours (under a load of 50 g/cm$^2$).

EXAMPLE 19

Water-swellable crosslinked polymer composition (16) of Example 16 was classified with a sieve of 850 μm. As a result, the ratio of passing through the sieve of 850 μm was 91.5 wt %. What passed through the sieve of 850 μm was regarded as water-swellable crosslinked polymer composition (19) according to the present invention, in which the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. The saltwater absorption capacity in 1 hour (under a load of 50 g/cm$^2$) of this composition was measured. As a result, it was 42.8 g/g. In addition, the saltwater absorption capacity in 4 hours (under a load of 50 g/cm$^2$) was 48.4 g/g.

EXAMPLE 20

Water-swellable crosslinked polymer composition (17) of Example 17 was classified with a sieve of 850 μm. As a result, the ratio of passing through the sieve of 850 μm was 92.9 wt %. What passed through the sieve of 850 μm was regarded as water-swellable crosslinked polymer composition (20) according to the present invention, in which the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. The saltwater absorption capacity in 1 hour (under a load of 50 g/cm$^2$) of this composition was measured. As a result, it was 43.5 g/g. In addition, the saltwater absorption capacity in 4 hours (under a load of 50 g/cm$^2$) was 47.8 g/g.

EXAMPLE 21

Water-swellable crosslinked polymer composition (18) of Example 18 was classified with a sieve of 850 μm. As a result, the ratio of passing through the sieve of 850 μm was 95.4 wt %. What passed through the sieve of 850 μm was regarded as water-swellable crosslinked polymer composition (21) according to the present invention, in which the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. The saltwater absorption capacity in 1 hour (under a load of 50 g/cm$^2$) of this composition was measured. As a result, it was 39.2 g/g. In addition, the saltwater absorption capacity in 4 hours (under a load of 50 g/cm$^2$) was 49.7 g/g.

EXAMPLE 22

One hundred and forty-five parts of basic particulate gel (1) of basicity in water, as obtained in Referential Example 14, and 100 parts of acid particulate gel (3) of acidity in water, as obtained in Referential Example 13, were blended in a kneader, and the resultant blend was caused to pass through a meat chopper, thus obtaining a blended and unified product. This blend was dried in a hot-air drier of 60° C. for 1 hour, and then pulverized with a roll mill pulverizer having a roll setting gap of 0.3 mm, and then caused to pass through a wire mesh of 850 μm, thus obtaining water-swellable crosslinked polymer composition (22) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The ratio of passing through the sieve of 850 μm was 96.8 wt %. The resultant composition exhibited a saltwater absorption capacity of 41.7 g/g in 1 hour (under a load of 50 g/cm$^2$), a saltwater absorption capacity of 52.5 g/g in 4 hours (under a load of 50 g/cm$^2$), a saltwater absorption speed of 34 seconds, a saltwater absorption capacity of 61.2 g/g under a load of 3.5 g/cm$^2$ in 10 hours, a saltwater absorption capacity of 39.1 g/g under a load of 3.5 g/cm$^2$ in 5 minutes, and further, a saltwater absorption capacity of 54.7 g/g under a load of 21 g/cm$^2$ in 10 hours, and a saltwater absorption capacity of 33.0 g/g under a load of 21 g/cm$^2$ in 5 minutes.

EXAMPLE 23

Water-swellable crosslinked polymer composition (23) according to the present invention was obtained in the same way as of Example 22 except that the acid particulate gel of acidity in water was changed to acid particulate gel (1) as obtained in Referential Example 11. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 44.2 g/g in 1 hour (under a load of 50 g/cm$^2$), a saltwater absorption capacity of 49.0 g/g in 4 hours (under a load of 50 g/cm$^2$), a saltwater absorption speed of 50 seconds, a saltwater absorption capacity of 60.5 g/g under a load of 3.5 g/cm$^2$ in 10 hours, a saltwater absorption capacity of 33.2 g/g under a load of 3.5 g/cm$^2$ in 5 minutes, and further, a saltwater absorption capacity of 53.9 g/g under a load of 21 g/cm$^2$ in 10 hours, and a saltwater absorption capacity of 28.4 g/g under a load of 21 g/cm$^2$ in 5 minutes.

EXAMPLE 24

One hundred and forty-five parts of basic particulate gel (1) of basicity in water, as obtained in Referential Example 14, and 100 parts of acid particulate gel (3) of acidity in water, as obtained in Referential Example 13, were blended in a kneader, and the resultant blend was caused to pass through a meat chopper, thus obtaining a blended and unified product. This blend was dried in a hot-air drier of 60° C. for 1 hour, and then pulverized with a roll mill pulverizer having a roll setting gap of 0.2 mm, and then caused to pass through a wire mesh of 850 μm, thus obtaining water-swellable crosslinked polymer composition (24) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The ratio of passing through the sieve of 850 μm was 96.0 wt %. The resultant composition exhibited a saltwater absorption capacity of 46.8 g/g in 1 hour (under a load of 50 g/cm$^2$), a saltwater absorption capacity of 51.7 g/g in 4 hours (under a load of 50 g/cm$^2$), a saltwater absorption speed of 30 seconds, a saltwater absorption capacity of 60.5 g/g under a load of 3.5 g/cm$^2$ in 10 hours, a saltwater absorption capacity of 40.3 g/g under a load of 3.5 g/cm$^2$ in 5 minutes, and further, a saltwater absorption capacity of 55.4 g/g under a load of 21 g/cm$^2$ in 10 hours, and a saltwater absorption capacity of 35.2 g/g under a load of 21 g/cm$^2$ in 5 minutes.

EXAMPLE 25

Water-swellable crosslinked polymer composition (25) according to the present invention was obtained in the same way as of Example 24 except that the acid particulate gel of acidity in water was changed to acid particulate gel (1) as obtained in Referential Example 11. In the resultant water-swellable crosslinked polymer composition, the water-swellable crosslinked polymer of basicity in water and the water-swellable crosslinked polymer of acidity in water were unified with each other, and part of acid groups of the water-swellable crosslinked polymer of acidity in water were neutralized with the water-swellable crosslinked polymer of basicity in water. This composition exhibited a saltwater absorption capacity of 43.4 g/g in 1 hour (under a load of 50 g/cm$^2$), a saltwater absorption capacity of 49.9 g/g in 4 hours (under a load of 50 g/cm$^2$), a saltwater absorption speed of 45 seconds, a saltwater absorption capacity of 59.2 g/g under a load of 3.5 g/cm$^2$ in 10 hours, a saltwater absorption capacity of 33.2 g/g under a load of 3.5 g/cm$^2$ in 5 minutes, and further, a saltwater absorption capacity of 53.2 g/g under a load of 21 g/cm$^2$ in 10 hours, and a saltwater absorption capacity of 29.3 g/g under a load of 21 g/cm$^2$ in 5 minutes.

EXAMPLE 26

Fifty parts of water-swellable crosslinked polymer (6) of acidity in water, as obtained in Referential Example 8, and 50 parts of water-swellable crosslinked polymer (2) of basicity in water, as obtained in Referential Example 7, were placed into a cup of 200 ml, and then blended while 5 parts of deionized water was gradually dropped thereto. The resultant blend was dried at 80° C. for 30 minutes, thus obtaining water-swellable crosslinked polymer composition (26) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The result of measuring the saltwater absorption capacity in 60 minutes of this composition was 28.1 g/g.

EXAMPLE 27

Fifty parts of water-swellable crosslinked polymer (6) of acidity in water, as obtained in Referential Example 8, and 50 parts of water-swellable crosslinked polymer (2) of basicity in water, as obtained in Referential Example 7, were placed into a cup of 200 ml, and then blended while 10 parts of deionized water was gradually dropped thereto. The resultant blend was dried at 80° C. for 30 minutes, thus obtaining water-swellable crosslinked polymer composition (27) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. The result of measuring the saltwater absorption capacity in 60 minutes of this composition was 28.4 g/g.

REFERENTIAL EXAMPLE 15

First, 2,500 g of 30% polyethylenimine (trade name: Epomin P-1000, made by Nippon Shokubai Co., Ltd.) was placed into a beaker of 5 liters as furnished with a stirrer to stir the contents. Next, a crosslinking agent solution was added thereto under stirring, wherein the crosslinking agent solution was prepared by dissolving 75 g of N,N'-methylenebisacrylamide (made by Nitto Chemical Industry Co., Ltd.) (crosslinking agent) into a mixed solvent of 400 g of pure water and 400 g of methanol. Then, the resultant mixture was stirred for 1 minute to obtain a homogeneous solution. Thereafter, the vessel was sealed, and then placed into a thermostat of 60° C. to carry out a reaction. After 3 hours, the system temperature was cooled down to room temperature, and the resultant lumped gel was pulverized with a meat chopper (rooster =3.1 mm), thus obtaining basic particulate gel (2) with an average particle diameter of 170 μm. This gel had a solid content of 26.5% and an extractable content of 3.5%.

REFERENTIAL EXAMPLE 16

First, 2,500 g of 30% polyethylenimine (trade name: Epomin P-1000, made by Nippon Shokubai Co., Ltd.) was placed into a beaker of 5 liters as furnished with a stirrer to stir the contents. Next, a crosslinking agent solution was added thereto under stirring, wherein the crosslinking agent solution was prepared by dissolving 75 g of ethylene glycol diglycidyl ether (trade name: Denacol EX-810, made by Nagase Chemicals, Ltd.) (crosslinking agent) into 725 g of water. Then, the resultant mixture was stirred for 1 minute to obtain a homogeneous solution. Thereafter, the vessel was sealed, and then placed into a thermostat of 60° C. to carry out a reaction. After 3 hours, the system temperature was cooled down to room temperature, and the resultant lumped gel was pulverized with a meat chopper (rooster=3.1 mm), thus obtaining basic particulate gel (3) with an average particle diameter of 180 μm. This gel had a solid content of 26.5% and an extractable content of 6.3%.

REFERENTIAL EXAMPLE 17

First, 70.00 parts of acrylic acid, 0.60 parts of N,N'-methylenebisacrylamide (copolymerizable crosslinking agent), and 274.84 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.12 parts of 10 weight % aqueous 2,2'-azobis(2-amidinopropane) dihydrochloride solution, 0.7 part of 10 weight % aqueous hydrogen peroxide solution, and 1.75 parts of 1 weight % aqueous L-ascorbic acid solution were added under stirring. As a result, after 3 minutes, a polymerization reaction got started, and after 25 minutes, the reaction system reached the peak temperature. Thirty minutes after the polymerization temperature reached its peak, the resultant hydrogelled crosslinked polymer was got out and then caused to pass through a meat chopper, thus obtaining a hydrogelled crosslinked polymer as finely divided. This polymer was dried in a hot-air drier of 150° C. for 1 hour. The resultant dried product was pulverized with a laboratory pulverizer, and the resultant pulverized product was sieved with a wire mesh of 850 μm in mesh opening size to separate what passed through it, thus obtaining water-swellable crosslinked polymer (7) of acidity in water. This polymer had a swelling capacity of 11.9 g/g for pure water, a water content of 2.0 wt %, and an extractable content of 2.7%, and comprised particles of 850~500 μm in the ratio of 36.3 wt %, particles of 500~300 μm in the ratio of 42.5 wt %, particles of 300~150 μm in the ratio of 20.3 wt %, and particles of not larger than 150 μm in the ratio of 0.9 wt %, and further had an average particle diameter of 430 μm.

EXAMPLE 28

First, 2,450 g of basic particulate gel (2), as obtained in Referential Example 15, was placed into a kneader of 10 liters, to which 650 g of polymer (water content: 1.9%) was then uniformly added at room temperature under stirring at 40 rpm, wherein the polymer was prepared by hot-air-drying water-swellable crosslinked polymer (5) of acidity in water, as obtained in Referential Example 6, at 150° C. for 60 minutes, and pulverizing the dried product, and sieving the pulverized product with a wire mesh of 850 μm to separate what passed through it. Thereafter, they were stirred for 10 minutes. The resultant blend was hot-air-dried at 80° C. for 2 hours, and then inorganic fine particles (trade name: Aerosil R972, made by Nippon Aerosil Co., Ltd.), were added to the dried product in the ratio of 0.3% (relative to the dried product), and they were well blended so that the inorganic fine particles could uniformly be dispersed. The resultant blend was pulverized with a laboratory pulverizer so that the pulverized product could pass through a wire mesh of 850 μm, thus obtaining water-swellable crosslinked polymer composition (28). This composition exhibited saltwater absorption capacities of 43 g/g and 48 g/g in 4 hours and in 20 hours respectively (under a load of 50 g/cm$^2$).

EXAMPLES 29 TO 38

In the combinations of Table 1, basic particulate gel (2) or (3) (100 parts in terms of solid content), as obtained in Referential Example 15 or 16, was placed into a kneader of 10 liters, to which 100 parts, 122 parts, 150 parts, 185 parts, or 233 parts of water-swellable crosslinked polymer (7) of acidity in water, as obtained in Referential Example 17, was then uniformly added at room temperature under stirring at 40 rpm. Thereafter, they were stirred for 10 minutes. The resultant blend was hot-air-dried at 80° C. for 2 hours, and then inorganic fine particles (trade name: Aerosil R972, made by Nippon Aerosil Co., Ltd.) were added to the dried product in the ratio of 0.3% (relative to the dried product), and they were well blended so that the inorganic fine particles could uniformly be dispersed. The resultant blend was pulverized with a laboratory pulverizer so that the pulverized product could pass through a wire mesh of 850 μm, thus obtaining water-swellable crosslinked polymer compositions (29) to (38). The saltwater absorption capacities in 1 hour, in 4 hours and in 20 hours respectively (under a load of 50 g/cm$^2$) of these compositions are shown in Table 1.

TABLE 1

|  | Blending ratio of acid crosslinked polymer/basic crosslinked polymer | Basic crosslinked polymer No. | Acid crosslinked polymer No. | Saltwater absorption capacity (under a load of 50 g/cm$^2$) | | |
| --- | --- | --- | --- | --- | --- | --- |
|  |  |  |  | 1 hour (g/g) | 4 hours (g/g) | 20 hours (g/g) |
| Example 29 | 100/100 | (2) | (7) | 36.7 | 43.6 | 46.8 |
| Example 30 | 122/100 | (2) | (7) | 36.6 | 43.8 | 47.4 |
| Example 31 | 150/100 | (2) | (7) | 36.5 | 43.2 | 45.5 |
| Example 32 | 185/100 | (2) | (7) | 36.2 | 42.0 | 43.4 |
| Example 33 | 233/100 | (2) | (7) | 33.5 | 38.6 | 40.0 |

TABLE 1-continued

| | Blending ratio of acid crosslinked polymer/basic crosslinked polymer | Basic crosslinked polymer No. | Acid crosslinked polymer No. | Saltwater absorption capacity (under a load of 50 g/cm²) | | |
|---|---|---|---|---|---|---|
| | | | | 1 hour (g/g) | 4 hours (g/g) | 20 hours (g/g) |
| Example 34 | 100/100 | (3) | (7) | 34.6 | 41.6 | 43.6 |
| Example 35 | 122/100 | (3) | (7) | 35.0 | 42.3 | 43.8 |
| Example 36 | 150/100 | (3) | (7) | 35.2 | 41.8 | 43.3 |
| Example 37 | 185/100 | (3) | (7) | 34.2 | 40.1 | 41.1 |
| Example 38 | 233/100 | (3) | (7) | 32.5 | 37.1 | 38.0 |

Acid crosslinked polymer: water-swellable crosslinked polymer of acidity in water
Basic crosslinked polymer: water-swellable crosslinked polymer of basicity in water

REFERENTIAL EXAMPLE 18

An aqueous monomer solution was prepared by dissolving 270 g of acrylic acid, 0.4 g of methylenebisacrylamide, 0.547 g of sodium persulfate, and 0.157 g of 2-hydroxy-2-methylpropiophenone into 810 g of deionized water, and then degassed by blowing nitrogen in for 15 minutes. This aqueous monomer solution was poured into a shallow glass dish, and then irradiated with ultraviolet rays of 15 mW/cm² for 25 minutes to carry out polymerization, thus obtaining a crosslinked polyacrylic acid gel.

COMPARATIVE EXAMPLE 4

Ethylene glycol diglycidyl ether (trade name: "Denacol EX-810," made by Nagase Chemicals, Ltd.) was added, in the ratio of 1.5 mol %, to an aqueous polyethylenimine solution (trade name: "EPOMIN P-1000," made by Nippon Shokubai Co., Ltd.), as diluted to 10%, to carry out a reaction at 60° C. for 16 hours, thus obtaining a crosslinked polyethylenimine. This resultant crosslinked polyethylenimine had an extractable content of 32.9%. Then, 37.4 parts (in terms of solid content) of the resultant crosslinked polyethylenimine gel and 62.6 parts (in terms of solid content) of the solid content of the crosslinked polyacrylic acid gel, as obtained in Referential Example 18, were separately pulverized into fine pieces in extruders, and then extruded. The resultant mixture was caused to twice pass through a meat chopper, thus obtaining a kneaded product in which both gels were uniformly kneaded. The resultant kneaded product was dried at 60° C. in an oven for 16 hours, and then freeze-pulverized to separate particles of 850~150 μm, thus obtaining comparative water-swellable crosslinked polymer composition (4).

This composition exhibited a desalting amount of 0.29 g/g, and saltwater absorption capacities of 18.9 g/g, 25.6 g/g, and 29.6 g/g in 1 hour, in 4 hours, and in 20 hours respectively (under a load of 50 g/cm²), and further, absorption capacities of 13.6 g/g and 17.1 g/g in 1 hour and in 3 hours respectively under a load (under a load of 50 g/cm²).

COMPARATIVE EXAMPLE 5

Ethylene glycol diglycidyl ether (trade name: "Denacol EX-810," made by Nagase Chemicals, Ltd.) was added, in the ratio of 1.0 mol %, to an aqueous polyethylenimine solution (trade name: "EPOMIN P-1000," made by Nippon Shokubai Co., Ltd.), as diluted to 20%, to carry out a reaction at 60° C. for 16 hours, thus obtaining a crosslinked polyethylenimine. This resultant crosslinked polyethylenimine had an extractable content of 23.2%. Then, 37.4 parts (in terms of solid content) of the resultant crosslinked polyethylenimine gel and 62.6 parts (in terms of solid content) of the solid content of the crosslinked polyacrylic acid gel, as obtained in Referential Example 18, were separately pulverized into fine pieces in extruders, and then extruded. The resultant mixture was caused to twice pass through a meat chopper, thus obtaining a kneaded product in which both gels were uniformly kneaded. The resultant kneaded product was dried at 60° C. in an oven for 16 hours, and then freeze-pulverized to separate particles of 850~150 μm, thus obtaining comparative water-swellable crosslinked polymer composition (5).

This composition exhibited a desalting amount of 0.29 g/g, and saltwater absorption capacities of 25.8 g/g, 31.5 g/g, and 31.3 g/g in 1 hour, in 4 hours, and in 20 hours respectively (under a load of 50 g/cm²), and further, absorption capacities of 22.6 g/g and 23.0 g/g in 1 hour and in 3 hours respectively under a load (under a load of 50 g/cm²).

COMPARATIVE EXAMPLE 6

First, 2.4 g of ethylene glycol diglycidyl ether (trade name: Denacol EX-810, made by Nagase Chemicals, Ltd.) was added to 100 g of aqueous polyallylamine solution with a concentration of 10% (trade name: PAA-10C, made by Nitto Boseki Co., Ltd.) under stirring and room temperature conditions. Immediately thereafter, 18.6 g of crosslinked polyacrylic acid particles (water content: 2.0%), as obtained by sieving the product of Referential Example 17 into the range of 500~150 μm, were further mixed, and the resultant mixture was stirred until it gelled. Thereafter, the resultant gel was aged at 60° C. for 3 hours, and then pulverized coarsely, and then dried at 80° C. for 1 hour. The resultant dried product was pulverized with a laboratory pulverizer so that the pulverized product could pass through a wire mesh of 850 μm, thus obtaining comparative water-swellable crosslinked polymer composition (6). This composition exhibited a saltwater absorption capacity of 34.1 g/g in 4 hours (under a load of 50 g/cm²).

COMPARATIVE EXAMPLE 7

First, 2.4 g of ethylene glycol diglycidyl ether (trade name: Denacol EX810, made by Nagase Chemicals, Ltd.) was added to 100 g of aqueous polyallylamine solution with a concentration of 10% (trade name: PAA-10C, made by Nitto Boseki Co., Ltd.) under stirring and room temperature conditions. Immediately thereafter, 93.0 g (18.6 g in terms of solid content) of crosslinked polyacrylic acid gel, as swollen by adding water to crosslinked polyacrylic acid particles so as to have a solid content of 20%, were further mixed, and the resultant mixture was stirred until it gelled, wherein the crosslinked polyacrylic acid particles were obtained by sieving the product of Referential Example 17 into the range of 500~150 $\mu$m. Thereafter, the resultant gel was aged at 60° C. for 3 hours, and then pulverized coarsely, and then dried at 80° C. for 1 hour. The resultant dried product was pulverized with a laboratory pulverizer so that the pulverized product could pass through a wire mesh of 850 $\mu$m, thus obtaining comparative water-swellable crosslinked polymer composition (7). This composition exhibited a saltwater absorption capacity of 34.4 g/g in 4 hours (under a load of 50 g/cm$^2$) and a desalting amount of 0.28 g/g.

COMPARATIVE EXAMPLE 8

A crosslinking agent solution, as prepared by dissolving 2 g of N,N'-methylenebisacrylamide (made by Nitto Chemical Industry Co., Ltd.) (crosslinking agent) into a mixed solvent of 5 g of pure water and 15 g of methanol, was added to 66.7 g of aqueous polyethylenimine solution with a concentration of 30% (trade name: EPOMIN P-1000, made by Nippon Shokubai Co., Ltd.) under stirring. Immediately thereafter, 22 g of crosslinked polyacrylic acid particles, as obtained by sieving the product of Referential Example 17 into the range of 500~150 $\mu$m, were further mixed, and the resultant mixture was stirred until it gelled. Thereafter, the resultant gel was aged at 60° C. for 3 hours, and then pulverized coarsely, and then dried at 80° C. for 1 hour. Inorganic fine particles (trade name: Aerosil A-200, made by Nippon Aerosil Co., Ltd.) were uniformly added to the resultant dried product in the ratio of 0.3 wt % relative to the weight of the dried product, and the resultant mixture was pulverized with a laboratory pulverizer so that the pulverized product could pass through a wire mesh of 850 $\mu$m, thus obtaining comparative water-swellable crosslinked polymer composition (8). This composition exhibited a saltwater absorption capacity of 32.2 g/g in 4 hours (under a load of 50 g/cm$^2$).

COMPARATIVE EXAMPLE 9

A crosslinking agent solution, as prepared by dissolving 1.6 g of N,N'-methylenebisacrylamide (made by Nitto Chemical Industry Co., Ltd.) (crosslinking agent) into a mixed solvent of 3 g of pure water and 12 g of methanol, was added to 53.3 g of aqueous polyethylenimine solution with a concentration of 30% (trade name: EPOMIN P-1000, made by Nippon Shokubai Co., Ltd.) under stirring. Immediately thereafter, 26.4 g of crosslinked polyacrylic acid particles, as obtained by sieving the product of Referential Example 17 into the range of 500~150 $\mu$m, were further mixed, and the resultant mixture was stirred until it gelled. Thereafter, the resultant gel was aged at 60° C. for 3 hours, and then pulverized coarsely, and then dried at 80° C. for 1 hour. Inorganic fine particles (trade name: Aerosil A-200, made by Nippon Aerosil Co., Ltd.) were uniformly added to the resultant dried product in the ratio of 0.3 wt % relative to the weight of the dried product, and the resultant mixture was pulverized with a laboratory pulverizer so that the pulverized product could pass through a wire mesh of 850 $\mu$m, thus obtaining comparative water-swellable crosslinked polymer composition (9). This composition exhibited a saltwater absorption capacity of 33.0 g/g in 4 hours (under a load of 50 g/cm$^2$).

EXAMPLE 39

A blend was prepared by blending 60 parts (in terms of solid content) of crosslinked polyacrylic acid hydrogel (as polymerized with the same composition as of Referential Example 5 and pulverized into an average particle diameter of 340 $\mu$m with a meat chopper as furnished with a plate having apertures of 4.5 mm) and 40 parts (in terms of solid content) of crosslinked polyethylenimine hydrogel (as crosslinked with the same composition as of Referential Example 15 and pulverized into an average particle diameter of 150 $\mu$m with a meat chopper as furnished with a plate having apertures of 2.4 mm) at 40 rpm in a kneader for 5 minutes. The resultant blend was hot-air-dried at 80° C. for 1 hour. Inorganic fine particles (trade name: A-200, made by Nippon Aerosil Co., Ltd.) were uniformly added to the resultant dried product in the ratio of 0.3 wt %, and the resultant blend was pulverized so that the pulverized product could pass through a wire mesh of 850 $\mu$m, thus obtaining water-swellable crosslinked polymer composition (39). This composition exhibited a desalting amount of 0.41 g/g in 4 hours, and saltwater absorption capacities of 39.0 g/g, 44.4 g/g, and 46.4 g/g in 1 hour, in 4 hours, and in 20 hours respectively (under a load of 50 g/cm$^2$).

EXAMPLE 40

Water-swellable crosslinked polymers of basicity in water according to the present invention, as obtained in Referential Examples 10, 15 and 16, had extractable contents of 3.2%, 3.5% and 6.3% respectively. In addition, water-swellable crosslinked polymers of acidity in water according to the present invention, as obtained in Referential Examples 1, 2, 3, 5, 6 and 17, had extractable contents of 2.5%, 8.5% 2.7%, 2.7%, 2.7% and 2.7% respectively. That it is important that both the water-swellable crosslinked polymer of basicity in water and the water-swellable crosslinked polymer of acidity in water have an extractable content of not more than 10% when blended in a hydrogelled state is, for example, clear from a fact that the saltwater absorption capacities in 1 hour (under a load of 50 g/cm$^2$) of the water-swellable crosslinked polymer compositions, as obtained in Examples 12, 29, 34 and 39 according to the present invention, all can achieve values of not less than 33.0 g/g, whereas those of comparative water-swellable crosslinked polymer compositions (4) and (5) of Comparative Examples 4 and 5 are less than such values.

EXAMPLE 41

First, 1,000 g of 30% polyethylenimine (trade name: Epomin P-1000, made by Nippon Shokubai Co., Ltd.) was placed into a beaker of 2 liters as furnished with THREE-ONE MOTORS to stir the contents. Next, a crosslinking agent solution was added thereto under stirring, wherein the crosslinking agent solution was prepared by dissolving 18 g of N,N'-methylenebisacrylamide (made by Nitto Chemical Industry Co., Ltd.) (crosslinking agent) into a mixed solvent of 100 g of pure water and 200 g of methanol. Then, the resultant mixture was stirred for 1 minute to obtain a homogeneous solution. Thereafter, the vessel was sealed, and then placed into a thermostat of 60° C. to carry out a reaction. After 3 hours, the system temperature was allowed to cool down to room temperature, and the resultant lumped gel was pulverized with a meat chopper, as furnished with a plate having apertures of 3.1 mm, so that the average gel particle diameter would be 150 $\mu$m. Next, a blend was prepared by blending 50 parts (in terms of solid content) of the resultant pulverized product of crosslinked polyethylenimine hydrogel (having an extractable content of 7.5%) and 50 parts (in terms of solid content) of crosslinked polyacrylic acid hydrogel with an average gel particle diameter of 300 μm (as polymerized with the same composition as of Referential Example 5 and pulverized with a meat chopper as furnished with a plate having apertures of 4.2 mm) at 40 rpm in a kneader for 5 minutes. The resultant blend was hot-air-dried at 80° C. for 1 hour. Inorganic fine particles (trade name: A-200, made by Nippon Aerosil Co., Ltd.) were uniformly added to the resultant dried product in the ratio of 0.5 wt %, and the resultant blend was pulverized so that the pulverized product could pass through a wire mesh of 850 μm, thus obtaining water-swellable crosslinked polymer composition (41). This composition exhibited saltwater absorption capacities of 37.0 g/g, 45.0 g/g, and 47.6 g/g in 1 hour, in 4 hours, and in 20 hours respectively (under a load of 50 g/cm$^2$), and a desalting amount of 0.41 g/g.

COMPARATIVE EXAMPLE 10

The hydrogel, as obtained by blending in the kneader in Example 41, was further kneaded and extruded with an extruder until becoming fine particles, and the resultant kneaded product was hot-air-dried at 80° C. for 1 hour. Inorganic fine particles (trade name: A-200, made by Nippon Aerosil Co., Ltd.) were uniformly added to the resultant dried product in the ratio of 0.5 wt %, and the resultant mixture was pulverized so that the pulverized product could pass through a wire mesh of 850 μm, thus obtaining comparative water-swellable crosslinked polymer composition (10). This composition exhibited saltwater absorption capacities of 29.0 g/g, 35.7 g/g, and 40.0 g/g in 1 hour, in 4 hours, and in 20 hours respectively (under a load of 50 g/cm$^2$), and a desalting amount of 0.28 g/g.

EXAMPLE 42

An aqueous monomer solution was prepared by charging 900.0 g of acrylic acid, 7.69 g of N,N'-methylenebisacrylamide, and 3,591.3 g of deionized water into a lidded polypropylene-made adiabatic polymerization reactor of 5 liters in capacity having a thermometer and a nitrogen-introducing tube. Next, the inside of the above reactor was displaced with nitrogen over a period of 1 hour while the temperature of the resultant aqueous monomer solution was kept in the range of about 20 to about 23° C. Thereafter, 27.23 g of 10% aqueous 2,2'-azobis(2-amidinopropane) dihydrochloride solution, 8.99 g of 10% aqueous hydrogen peroxide solution, and 22.48 g of 1% aqueous L-ascorbic acid solution were added under stirring to initiate polymerization. As a result, after about 1 minute, the polymerization started, and the temperature rise and gelation of the aqueous monomer solution were observed. Static adiabatic polymerization was further continued for 1 hour, thus obtaining a hydrogelled crosslinked polymer with a solid content of 18.8%.

Next, the resultant hydrogelled crosslinked polymer was got out of the polymerization reactor and then cut with a meat chopper of 9.5 mm in rooster diameter, thus obtaining hydrogel particles with an average particle diameter of 1,000 μm. Next, 500 g of the hydrogel particles were spread into the size of 27 cm×19 cm on a wire mesh of 100 μm in mesh opening size and then heated at 150° C. in a hot-air drying oven for 15 minutes. After being heated, the particles were further pulverized and then caused to pass through a wire mesh of 850 μm, thus obtaining water-swellable crosslinked polymer (8) of acidity in water, which polymer had an average particle diameter of 350 μm, a water content of 1.6%, and an extractable content of 3.3%.

EXAMPLE 43

Water-swellable crosslinked polymer (9) of acidity in water, having an average particle diameter of 350 μm, a water content of 3.0%, and an extractable content of 2.9%, was obtained in the same way as of Example 42 except that after carrying out the polymerization in the same way, the time for which the resultant hydrogelled crosslinked polymer was heated was changed to 5 minutes.

EXAMPLE 44

Water-swellable crosslinked polymer (10) of acidity in water, having an average particle diameter of 350 μm, a water content of 1.6%, and an extractable content of 3.5%, was obtained in the same way as of Example 42 except that after carrying out the polymerization in the same way, the time for which the resultant hydrogelled crosslinked polymer was heated was changed to 20 minutes.

EXAMPLE 45

Water-swellable crosslinked polymer (11) of acidity in water, having an average particle diameter of 350 μm, a water content of 1.3%, and an extractable content of 3.6%, was obtained in the same way as of Example 42 except that after carrying out the polymerization in the same way, the time for which the resultant hydrogelled crosslinked polymer was heated was changed to 30 minutes.

EXAMPLE 46

Water-swellable crosslinked polymer (12) of acidity in water, having an average particle diameter of 350 μm, a water content of 0.9%, and an extractable content of 3.8%, was obtained in the same way as of Example 42 except that after carrying out the polymerization in the same way, the time for which the resultant hydrogelled crosslinked polymer was heated was changed to 60 minutes.

EXAMPLE 47

Water-swellable crosslinked polymer (13) of acidity in water, having an average particle diameter of 350 μm, a water content of 4.3%, and an extractable content of 2.4%, was obtained in the same way as of Example 42 except that after carrying out the polymerization in the same way, the resultant hydrogelled crosslinked polymer was heated at 100° C. for 60 minutes.

EXAMPLE 48

Water-swellable crosslinked polymer (14) of acidity in water, having an average particle diameter of 350 μm, a water content of 4.6%, and an extractable content of 2.4%, was obtained in the same way as of Example 42 except that after carrying out the polymerization in the same way, the resultant hydrogelled crosslinked polymer was heated at 120° C. for 30 minutes.

EXAMPLE 49

Water-swellable crosslinked polymer (15) of acidity in water, having an average particle diameter of 350 μm, a water content of 1.2%, and an extractable content of 2.4%, was obtained in the same way as of Example 42 except that after carrying out the polymerization in the same way, the resultant hydrogelled crosslinked polymer was heated at 120° C. for 60 minutes.

EXAMPLE 50

Water-swellable crosslinked polymer (16) of acidity in water, having an average particle diameter of 350 μm, a water content of 0.9%, and an extractable content of 2.6%, was obtained in the same way as of Example 42 except that after carrying out the polymerization in the same way, the resultant hydrogelled crosslinked polymer was heated at 120° C. for 2 hours.

EXAMPLE 51

Water-swellable crosslinked polymer (17) of acidity in water, having an average particle diameter of 350 µm, a water content of 0.5%, and an extractable content of 3.5%, was obtained in the same way as of Example 42 except that after carrying out the polymerization in the same way, the resultant hydrogelled crosslinked polymer was heated at 160° C. for 30 minutes.

EXAMPLE 52

Water-swellable crosslinked polymer (18) of acidity in water, having an average particle diameter of 350 µm, a water content of 0.3%, and an extractable content of 3.5%, was obtained in the same way as of Example 42 except that after carrying out the polymerization in the same way, the resultant hydrogelled crosslinked polymer was heated at 170° C. for 30 minutes.

EXAMPLE 53

Water-swellable crosslinked polymer (19) of acidity in water, having an average particle diameter of 350 µm, a water content of 0.2%, and an extractable content of 3.4%, was obtained in the same way as of Example 42 except that after carrying out the polymerization in the same way, the resultant hydrogelled crosslinked polymer was heated at 180° C. for 30 minutes.

REFERENTIAL EXAMPLE 19

First, 2,500 g of 30% aqueous polyethylenimine solution (trade name: EPOMIN P-1000, made by Nippon Shokubai Co., Ltd.) was placed into a reaction vessel of 5 liters as furnished with stirring vanes. Next, an aqueous crosslinking agent solution was added to the aqueous polyethylenimine solution under stirring, wherein the crosslinking agent solution was prepared by dissolving 75 g of methylenebisacrylamide into 725 g of pure water. Then, the resultant mixture was stirred for about I minute to obtain a homogeneous solution. Thereafter, the vessel was heated to carry out a reaction at a temperature of 60° C. for 3 hours. After 3 hours, the system temperature was cooled down to room temperature, and the resultant lumped gel was pulverized with a meat chopper (rooster=2.4 mm), thus obtaining basic particulate gel (4). This gel had an average particle diameter of 150 µm, a solid content of 25.0% and an extractable content of 3.6%.

EXAMPLE 54

Figure 2:
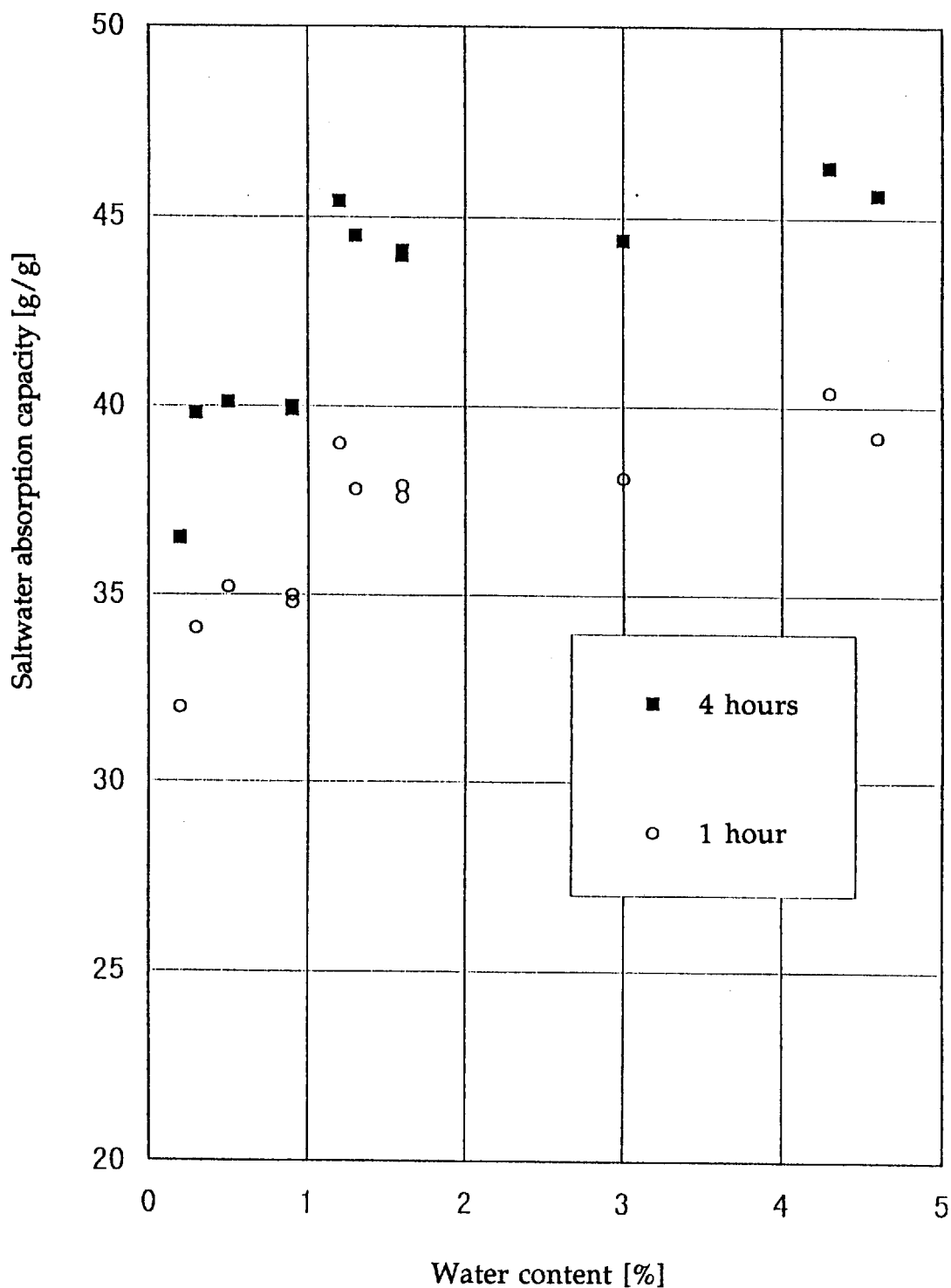
FIG. 2 is a graph showing the results of Example 54.

Basic particulate gel (4) (100 parts in terms of solid content), as obtained in Referential Example 19, was placed into a kneader of 10 liters, to which 100 parts of each of water-swellable crosslinked polymers (8) to (19) of acidity in water, as obtained in Examples 42 to 53, was then uniformly added at room temperature under stirring at 40 rpm. Thereafter, they were stirred for 10 minutes. The resultant blend was hot-air-dried 80° C. for 2 hours, and then inorganic fine particles (trade name: REOLOSIL QS-20, made by Tokuyama Corporation) were added in the ratio of 0.3% to the dried product, and they were well blended so that the inorganic fine particles could uniformly be dispersed. The resultant blend was pulverized with a laboratory pulverizer so that the pulverized product could pass through a wire mesh of 850 µm, thus obtaining water-swellable crosslinked polymer compositions. The saltwater absorption capacities in 1 hour and in 4 hours respectively (under a load of 50 g/cm$^2$) of these compositions are shown in Table 2 and FIG. 2.

TABLE 2

|  | Water-swellable crosslinked polymer of acidity in water | | Saltwater absorption capacity of water-swellable crosslinked polymer composition | |
| --- | --- | --- | --- | --- |
|  | Water content (%) | Extractable content (%) | 1 hour (g/g) | 4 hours (g/g) |
| Example 42 | 1.6 | 3.3 | 37.6 | 44.0 |
| Example 43 | 3.0 | 2.9 | 38.1 | 44.4 |
| Example 44 | 1.6 | 3.5 | 37.9 | 44.1 |
| Example 45 | 1.3 | 3.6 | 37.8 | 44.5 |
| Example 46 | 0.9 | 3.8 | 34.8 | 39.9 |
| Example 47 | 4.3 | 2.4 | 40.4 | 46.3 |
| Example 48 | 4.6 | 2.4 | 39.2 | 45.6 |
| Example 49 | 1.2 | 2.4 | 39.0 | 45.4 |
| Example 50 | 0.9 | 2.6 | 35.0 | 40.0 |
| Example 51 | 0.5 | 3.5 | 35.2 | 40.1 |
| Example 52 | 0.3 | 3.5 | 34.1 | 39.8 |
| Example 53 | 0.2 | 3.4 | 32.0 | 36.5 |

REFERENTIAL EXAMPLE 20

First, 68.97 parts of acrylic acid, 0.74 parts of N,N'-methylenebisacrylamide (crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 1 weight % aqueous L-ascorbic acid solution were added under stirring. As a result, after 4.5 minutes, a polymerization reaction got started, and after 21 minutes, the reaction system reached the peak temperature. Thirty minutes after the polymerization temperature reached its peak, the resultant hydrogelled polyacrylic acid was got out, thus obtaining hydrogelled water-swellable crosslinked polymer (20) of acidity in water. The amount of residual acrylic acid in this polymer was 7,610 ppm.

REFERENTIAL EXAMPLE 21

First, 69.11 parts of acrylic acid, 0.59 parts of N,N'-methylenebisacrylamide (crosslinking agent), and 275.8 parts of water were mixed. The resultant mixture was degassed with nitrogen gas for 60 minutes and then put into an airtight vessel possible to open and close, and the displacement of the internal air of the reaction system with nitrogen was continued with the liquid temperature kept at 23° C. under the nitrogen atmosphere. Next, 2.1 parts of 10 weight % aqueous 2,2'-azobis(2-amidinopropane) dihydrochloride solution, 0.7 part of 10 weight % aqueous hydrogen peroxide solution, and 1.7 parts of 10 weight % aqueous L-ascorbic acid solution were added under stirring. As a result, after 6 minutes, a polymerization reaction got started, and after 32 minutes, the reaction system reached the peak temperature. Thirty minutes after the polymerization temperature reached its peak, the resultant hydrogelled polyacrylic acid was got out, thus obtaining hydrogelled water-swellable crosslinked polymer (21) of acidity in water. The amount of residual acrylic acid in this polymer was 5,790 ppm.

REFERENTIAL EXAMPLE 22

First, 10 liters of cyclohexane solution, containing 100 g of inorganic particles (trade name: Aerosil R972, made by Nippon Aerosil Co., Ltd.), was placed into a stainless bottle of 20 liters with a dropping funnel, a stirrer, a thermometer, and a reflux condenser, and then stirred at room temperature. Next, 363 g of 50% aqueous solution of ethylene glycol diglycidyl ether (trade name: Denacol EX810, made by Nagase Chemicals, Ltd.) (crosslinking agent) was added under stirring to an aqueous polyethylenimine solution having been cooled to 0° C. beforehand and comprising 5,636 g of 30% polyethylenimine (trade name: Epomin P-1000, made by Nippon Shokubai Co., Ltd.) and 4,000 g of pure water, thus preparing an aqueous solution containing a crosslinking agent and polyethylenimine. Then, this solution was added to the above cyclohexane solution at room temperature under stirring. Under stirring, the temperature of the system was gradually raised to 65° C., and the reaction was carried out at 65° C. for 3 hours. Then, the temperature of the system was cooled to room temperature, and the resultant spherical hydrogel was filtrated by suction, and then immersed in a large amount of pure water for 24 hours, and then filtrated, and then dried under decompression at 60° C. for 20 hours, thus obtaining water-swellable crosslinked polymer (5) of basicity in water, which polymer had a water content of 15%.

REFERENTIAL EXAMPLE 23

First, 20 parts of 10% aqueous polyallylamine solution (trade name: PAA-10C, made by Nitto Boseki Co., Ltd.) was mixed with 0.5 parts of ethylene glycol diglycidyl ether (trade name: Denacol EX810, made by Nagase Chemicals, Ltd.) (crosslinking agent), and the resultant mixture was heated in an airtight vessel at 50° C. for 24 hours, whereby a crosslinked polyallylamine was obtained. The resultant crosslinked polyallylamine was cut into small pieces in a mixer, thus obtaining hydrogelled water-swellable crosslinked polymer (6) of basicity in water.

EXAMPLE 55

An amount of 23.5 parts of water-swellable crosslinked polymer (5) of basicity in water, as obtained in Referential Example 22, was added to 100 parts of hydrogelled water-swellable crosslinked polymer (20) of acidity in water, as obtained in Referential Example 20, in a kneader under stirring, and they were blended for 10 minutes. The resultant blend was caused to pass through a meat chopper of 3.1 mm in rooster diameter, and then dried in a hot-air drier of 80° C. for 1 hour. Thereafter, 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (55) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition had a water content of 18.4%, and the amount of residual acrylic acid in this composition was ND (nondetectable: less than 50 ppm). In addition, this composition exhibited saltwater absorption capacities of 24.5 g/g in 10 minutes and 36.4 g/g in 60 minutes after starting to absorb the liquid.

EXAMPLE 56

An amount of 23.5 parts of water-swellable crosslinked polymer (5) of basicity in water, as obtained in Referential Example 22, was added to 100 parts of hydrogelled water-swellable crosslinked polymer (21) of acidity in water, as obtained in Referential Example 21, in a kneader under stirring, and they were blended for 10 minutes. The resultant blend was caused to pass through a meat chopper of 3.1 mm in rooster diameter, and then dried in a hot-air drier of 80° C. for 1 hour. Thereafter, 100 parts of the resultant dried product was further blended with 0.5 parts of fine silica particles (trade name: Aerosil 200, made by Nippon Aerosil Co., Ltd.), and then pulverized with a laboratory pulverizer. The resultant pulverized product was sieved with a wire mesh of 850 μm in mesh opening size to separate what passed through it, thus obtaining water-swellable crosslinked polymer composition (56) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition had a water content of 18.6%, and the amount of residual acrylic acid in this composition was ND (nondetectable: less than 50 ppm). In addition, this composition exhibited saltwater absorption capacities of 22.3 g/g in 10 minutes and 33.6 g/g in 60 minutes after starting to absorb the liquid.

EXAMPLE 57

An amount of 150 parts of hydrogelled water-swellable crosslinked polymer (6) of basicity in water, as obtained in Referential Example 23, was added to 100 parts of hydrogelled water-swellable crosslinked polymer (21) of acidity in water, as obtained in Referential Example 21, and they were blended while being stirred in a kneader, and the resultant blend was caused to pass through a meat chopper of 3.1 mm in rooster diameter, and then dried in a hot-air drier of 80° C. for 1 hour, and then pulverized with a roll mill pulverizer. The resultant pulverized product was classified by sieving it with a wire mesh of 850 μm in mesh opening size to separate what passed through it, thus obtaining water-swellable crosslinked polymer composition (57) according to the present invention, in which the water-swellable crosslinked polymer of basicity in water and the water-swellable crosslinked polymer of acidity in water were unified with each other, and in which part of acid groups of the water-swellable crosslinked polymer of acidity in water were neutralized with the water-swellable crosslinked polymer of basicity in water. This composition had a water content of 8.6%, and the amount of residual acrylic acid in this composition had been reduced to 90 ppm. This composition exhibited saltwater absorption capacities of 32.1 g/g in 10 minutes and 45.5 g/g in 60 minutes after starting to absorb the liquid.

From the above Examples and Comparative Examples, it would be understood as follows. As to the compositions as obtained by blending both water-swellable crosslinked polymers under conditions where one of them is in a hydrogelled state in Examples 1 to 9, 11, and 28 to 40, the compositions as obtained by blending both water-swellable crosslinked polymers under conditions where both of them are in a hydrogelled state in Examples 10, 12 to 25, and 41, and the compositions as obtained by blending both dry water-swellable crosslinked polymers in the presence of water in Examples 26 and 27, all exhibit excellent property values when compared with the compositions as obtained by blending both dry water-swellable crosslinked polymers under dry conditions in Comparative Examples 2 and 3. In addition, Examples 6 to 38 and 55 to 57 and FIG. 1 demonstrate that the initial saltwater absorption capacity under a load is excellent. Examples 13 to 25 demonstrate that when both water-swellable crosslinked polymers are blended under conditions where both of them are in a gelled state, it is effective to the properties to adjust the gel particle diameter. Examples 55 to 57 demonstrate that the amount of residual monomer is reduced.

Comparative Examples 4 and 5 involve the use of water-swellable crosslinked polymers of which the extractable contents are high, while Examples 39 and 40 demonstrate that if water-swellable crosslinked polymers of which the extractable contents are low even if the compositions of these polymers are the same as those of water-swellable crosslinked polymers of which the extractable contents are high are used, then water-swellable crosslinked polymer compositions which are remarkably excellent in the saltwater absorption capacity and in the desalting amount are obtainable.

From the comparison of Example 41 with Comparative Example 10, it would be understood that a water-swellable crosslinked polymer composition which is remarkably excellent in the saltwater absorption capacity and in the desalting amount is obtainable by controlling the particle sizes of hydrogels of water-swellable crosslinked polymers and then blending both polymers so as not to apply too much force to them (in other words, blending both polymers under conditions where their particle shapes previous to blending were kept).

As is evident from the results of Example 54 and the results of Examples 29 to 38, it would be understood that water-swellable crosslinked polymer compositions which are excellent with regard to the absorption capacity for a physiological salt solution and to the saltwater absorption capacity in 4 hours are obtainable if a hydrogelled water-swellable crosslinked polymer of acidity in water is heated at a temperature of not lower than 100° C. so that the water content in the polymer will be in the range of 1 to 20 weight % (but not including 20 weight %) after heating. The reason therefor is not certain, but it would be inferred that there occurs some difference between forms of ionic bondings to the compound of basicity in water. Also from these results, it would be considered important in the present invention that the water-swellable crosslinked polymer particles of acidity in water are unified with the water-swellable crosslinked polymer particles of basicity in water through ionic bondings in a state where water is present between the particles.

INDUSTRIAL APPLICATION

The water-swellable crosslinked polymer composition, according to the present invention, can rapidly absorb salt water under loaded conditions, and further, exhibits excellent absorption capacity under a load. Accordingly, if the water-swellable crosslinked polymer composition according to the present invention is used as a water-absorbing agent for absorbent articles such as disposable diapers, the leakage can be remarkably decreased and their surfaces can be kept in a rustling dry state, even in the case of a long-term use.

What is claimed is:

1. A water-swellable crosslinked polymer composition, which comprises a blend of a water-swellable crosslinked polymer of acidity in water and a water-swellable crosslinked polymer of basicity in water, with the composition being characterized by exhibiting a saltwater absorption capacity of at least 50 g/g under a load of 3.5 g/cm$^2$ in 10 hours, and absorbing 60% of the 10-hour saltwater absorption capacity under the load of 3.5 g/cm$^2$ in less than 5 minutes.

2. A water-swellable crosslinked polymer composition, which comprises a blend of a water-swellable crosslinked polymer of acidity in water and a water-swellable crosslinked polymer of basicity in water, with the composition being characterized by exhibiting a saltwater absorption capacity of at least 40 g/g under a load of 21 g/cm$^2$ in 10 hours, and absorbing 60% of the 10-hour saltwater absorption capacity under the load of 21 g/cm$^2$ in less than 5 minutes.

3. A water-swellable crosslinked polymer composition, which comprises a blend of water-swellable crosslinked polymer particles of acidity in water and water-swellable crosslinked polymer particles of basicity in water, with the composition being characterized in that the water-swellable crosslinked polymer particles of acidity in water are unified with the water-swellable crosslinked polymer particles of basicity in water through ionic bondings in a state where water is present between the particles, and further characterized by exhibiting a saltwater absorption capacity of not less than 33 g/g in 60 minutes.

4. A water-swellable crosslinked polymer composition according to claim 3, wherein the water-swellable crosslinked polymer of acidity in water and the water-swellable crosslinked polymer of basicity in water are unified with each other, wherein each of the water-swellable crosslinked polymers is in a state of particles in the range of 1~1,000 μm.

5. A water-swellable crosslinked polymer composition, which comprises a blend of water-swellable crosslinked polymer particles of acidity in water and water-swellable crosslinked polymer particles of basicity in water, with the composition being characterized in that ionic bondings are formed in a state where water is present between the particles by neutralization of at least part of acid groups of the water-swellable crosslinked polymer particles of acidity in water with the water-swellable crosslinked polymer particles of basicity in water, and further characterized by exhibiting an absorption capacity of not less than 25 g/g under a load.

6. A water-swellable crosslinked polymer composition according to claim 3, which has a water content of 5~25 weight %.

7. A water-swellable crosslinked polymer composition according to claim 1, wherein the water-swellable crosslinked polymer of basicity in water is a crosslinked polyethylenimine or a crosslinked polyallylamine.

8. A water-swellable crosslinked polymer composition, which comprises a blend of a water-swellable crosslinked polymer of acidity in water and a water-swellable crosslinked polymer of basicity in water, with the composition being characterized in that the water-swellable crosslinked polymer of acidity in water is a crosslinked polyacrylic acid, and in that the water-swellable crosslinked polymer of basicity in water is a crosslinked polyethylenimine or a crosslinked polyallylamine, and further characterized by exhibiting a desalting amount of not less than 0.35 g/g.

9. A production process for a water-swellable crosslinked polymer composition including a blend of water-swellable crosslinked polymer particles of acidity in water and water-swellable crosslinked polymer particles of basicity in water, with the process being characterized by comprising the step of adding the water-swellable crosslinked polymer particles of basicity in water to the water-swellable crosslinked polymer particles of acidity in water, thereby neutralizing at least part of acid groups of the water-swellable crosslinked polymer particles of acidity in water to form ionic bondings in a state where water is present between the particles.

10. A production process for a water-swellable crosslinked polymer composition including a blend of a water-swellable crosslinked polymer of acidity in water and a water-swellable crosslinked polymer of basicity in water, with the process being characterized by comprising the step of blending the water-swellable crosslinked polymer of acidity in water and the water-swellable crosslinked polymer of basicity in water under conditions where at least one of the water-swellable crosslinked polymer of acidity in water and the water-swellable crosslinked polymer of basicity in water is in a hydrogelled state, and further characterized in that both the water-swellable crosslinked polymer of acidity in water and the water-swellable crosslinked polymer of basicity in water have an extractable content of not more than 10 weight % before blending.

11. A production process according to 10, wherein the water-swellable crosslinked polymer of acidity in water and the water-swellable crosslinked polymer of basicity in water are blended so that the applied force due to blending may be a facial pressure less than 50 kg/cm$^2$ or a linear pressure less than 25 kg/cm.

12. A production process according to 10, wherein the water-swellable crosslinked polymer of acidity in water is in a hydrogelled state before blending, when this polymer has an average gel particle diameter of 100~1,500 μm.

13. A production process according to 10, wherein the water-swellable crosslinked polymer of acidity in water has a water content of 1~20 weight % before blending, when this polymer has an average particle diameter of not less than 300 μm.

14. A production process according to claim 9, wherein the water-swellable crosslinked polymer of basicity in water is a crosslinked polyethylenimine or a crosslinked polyallylamine.

15. A production process for a water-swellable crosslinked polymer of acidity in water, comprising the steps of: carrying out aqueous solution polymerization of a polymerizable monomer in the presence of a copolymerizable crosslinking agent, wherein the polymerizable monomer contains at least one acid group selected from the group consisting of carboxylic acid groups, sulfonic acid groups, and phosphoric acid groups, and 80 to 100 mol % of the acid groups in the polymerizable monomer are present in the acid form; and heating the resultant hydrogelled polymer at a temperature of not lower than 100° C. so that the water content in the polymer will be in the range of 1 to 20 weight % (but not including 20 weight %); and further, if necessary, pulverizing the heated polymer.

16. A water-swellable crosslinked polymer composition according to claim 5, which has a water content of 5–25 weight %.

17. A water-swellable crosslinked polymer composition according to claim 2, wherein the water-swellable crosslinked polymer of basicity in water is a crosslinked polyethylenimine and/or a crosslinked polyallylamine.

18. A water-swellable crosslinked polymer composition according to claim 3, wherein the water-swellable crosslinked polymer of basicity in water is a crosslinked polyethylenimine and/or a crosslinked polyallylamine.

19. A water-swellable crosslinked polymer composition according to claim 5, where the water-swellable crosslinked polymer of basicity in water is a crosslinked polyethylenimine and/or a crosslinked polyallylamine.

20. A production process according to claim 10, wherein the water-swellable crosslinked polymer of basicity in water is a crosslinked polyethylenimine and/or a crosslinked polyallylamine.

21. The water-swellable crosslinked polymer composition of claim 1, wherein 50 to 100 mol % of acid groups in said water-swellable crosslinked polymer of acidity in water are present in the acid form.

22. The water-swellable crosslinked polymer composition of claim 1, wherein said composition has a swelling capacity for pure water of said water-swellable crosslinked polymer of basicity in water not less than 5 g/g.

23. The water-swellable crosslinked polymer composition of claim 1, wherein said water-swellable crosslinked polymer particles of acidity in water and said water-swellable crosslinked polymer particles of basicity in water are unified with each other through ionic bonds in a state where water is present between the particles.

24. The water-swellable crosslinked polymer composition of claim 2, wherein 50 to 100 mol % of acid groups in said water-swellable crosslinked polymer of acidity in water are present in the acid form.

25. The water-swellable crosslinked polymer composition of claim 2, wherein said composition has a swelling capacity for pure water of said water-swellable crosslinked polymer of basicity in water not less than 5 g/g.

26. The water-swellable crosslinked polymer composition of claim 2, wherein said water-swellable crosslinked polymer particles of acidity in water and said water-swellable crosslinked polymer particles of basicity in water are unified with each other through ionic bonds in a state where water is present between the particles.

27. The water-swellable crosslinked polymer composition of claim 3, wherein 50 to 100 mol % of acid groups in said water-swellable crosslinked polymer of acidity in water are present in the acid form.

28. The water-swellable crosslinked polymer composition of claim 3, wherein said composition has a swelling capacity for pure water of said water-swellable crosslinked polymer of basicity in water not less than 5 g/g.

29. The water-swellable crosslinked polymer composition of claim 5, wherein said water-swellable crosslinked polymer composition are particles.

30. The water-swellable crosslinked polymer composition of claim 8, wherein said water-swellable crosslinked polymer composition are particles.

31. The water-swellable crosslinked polymer composition of claim 9, wherein said water-swellable crosslinked polymer composition are particles.

* * * * *